US011690556B2

(12) United States Patent
Botzer et al.

(10) Patent No.: US 11,690,556 B2
(45) Date of Patent: *Jul. 4, 2023

(54) CLASSIFYING ECG SIGNALS

(71) Applicant: Biosense Webster (Israel) Ltd., Yokneam (IL)

(72) Inventors: Lior Botzer, Timrat (IL); Meir Bar-Tal, Haifa (IL); Elad Nakar, Timrat (IL); Noga Salomon, Karmiel (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 64 days.

This patent is subject to a terminal disclaimer.

(21) Appl. No.: 17/373,289

(22) Filed: Jul. 12, 2021

(65) Prior Publication Data

US 2021/0338131 A1  Nov. 4, 2021

Related U.S. Application Data

(62) Division of application No. 15/646,393, filed on Jul. 11, 2017, now Pat. No. 11,058,342.

(Continued)

(51) Int. Cl.
*A61B 5/316* (2021.01)
*A61B 5/00* (2006.01)
(Continued)

(52) U.S. Cl.
CPC ............. *A61B 5/316* (2021.01); *A61B 5/287* (2021.01); *A61B 5/352* (2021.01); *A61B 5/6852* (2013.01);
(Continued)

(58) Field of Classification Search
None
See application file for complete search history.

(56) References Cited

U.S. PATENT DOCUMENTS

2010/0191132 A1  7/2010  Jackson
2013/0226016 A1  8/2013  Narayan et al.
(Continued)

FOREIGN PATENT DOCUMENTS

EP  2 526 861 A1  11/2012
EP  2 901 923 A1  8/2015

OTHER PUBLICATIONS

European Search Report dated Dec. 11, 2017 from corresponding European Patent Application No. 17185772.5.

*Primary Examiner* — Catherine M Voorhees
*Assistant Examiner* — Elizabeth K So
(74) *Attorney, Agent, or Firm* — Lewis Roca Rothgerber Christie LLP

(57) ABSTRACT

A method, including receiving a bipolar signal from a pair of electrodes in proximity to a myocardium of a human subject, and receiving a unipolar signal from a selected one of the pair of electrodes. The method further includes delineating a window of interest (WOI) for the unipolar and bipolar signals, within the WOI computing local unipolar minimum derivatives of the unipolar signal, and times of occurrence of the local unipolar minimum derivatives, and within the WOI computing bipolar derivatives of the bipolar signal at the times of occurrence. The method also includes evaluating ratios of the bipolar derivatives to the local unipolar minimum derivatives, and when the ratios are greater than a preset threshold ratio value, assigning the times of occurrence as times of activation of the myocardium, counting a number of the times of activation; and classifying the unipolar signal according to the number.

9 Claims, 22 Drawing Sheets

Related U.S. Application Data

(60) Provisional application No. 62/373,465, filed on Aug. 11, 2016.

(51) Int. Cl.
*A61B 5/287* (2021.01)
*A61B 5/352* (2021.01)

(52) U.S. Cl.
CPC .......... *A61B 5/6869* (2013.01); *A61B 5/7264* (2013.01); *A61B 5/743* (2013.01); *A61B 2505/05* (2013.01)

(56) References Cited

U.S. PATENT DOCUMENTS

| | | |
|---|---|---|
| 2015/0208938 A1 | 7/2015 | Houben et al. |
| 2015/0245782 A1 | 9/2015 | Morland et al. |
| 2017/0214631 A1 | 7/2017 | Zhang et al. |

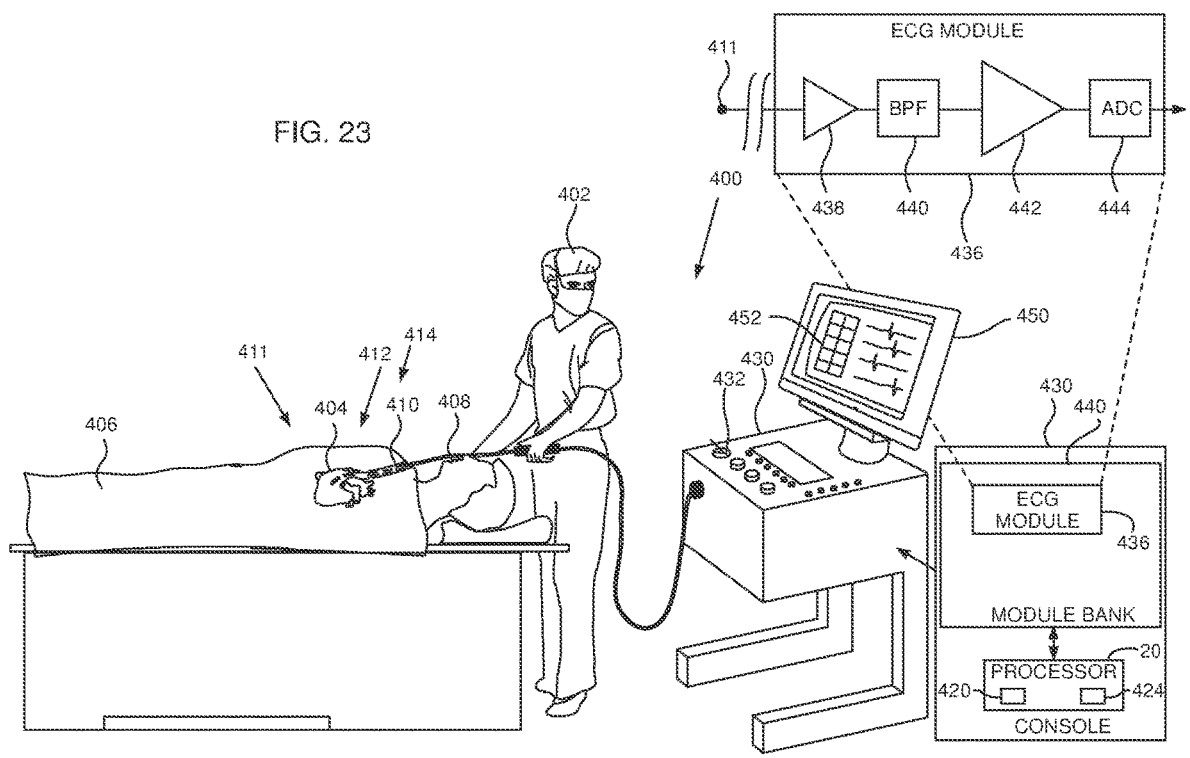

CLASSIFYING ECG SIGNALS

CROSS-REFERENCE TO RELATED APPLICATION(S)

This application is a divisional of U.S. patent application Ser. No. 15/646,393, filed Jul. 11, 2017, now U.S. Pat. No. 11,058,342, which claims the benefit of U.S. Provisional Patent Application 62/373,465, filed Aug. 11, 2016, the content of both of which is incorporated herein by reference. This application is related to U.S. patent application Ser. No. 15/646,373, filed Jul. 11, 2017, titled "Annotation of a Wavefront," now U.S. Pat. No. 10,383,534.

FIELD OF THE INVENTION

This invention relates generally to electrocardiograph (ECG) signals, and specifically to a method for classifying the signals.

BACKGROUND OF THE INVENTION

Mapping and imaging of the electrical signals in the heart is typically based on combining local activation time (LAT), as indicated by a catheter's ECG signals, with the spatial position of the signals. Such a method is used in the CARTO® 3 System, produced by Biosense Webster of Diamond Bar, Calif.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including receiving a bipolar signal from a pair of electrodes in proximity to a myocardium of a human subject, and receiving a unipolar signal from a selected one of the pair of electrodes. The method also includes delineating a window of interest (WOI) for the unipolar and bipolar signals, and within the WOI computing local unipolar minimum derivatives of the unipolar signal, and times of occurrence of the local unipolar minimum derivatives.

The method further includes, within the WOI, computing bipolar derivatives of the bipolar signal at the times of occurrence, evaluating ratios of the bipolar derivatives to the local unipolar minimum derivatives, and when the ratios are greater than a preset threshold ratio value, assigning the times of occurrence as times of activation of the myocardium, counting a number of the times of activation, and classifying the unipolar signal according to the number.

In a disclosed embodiment, when the bipolar derivatives are less than a preset bipolar derivative threshold, the times of occurrence are assigned as the times of activation of the myocardium.

In a further disclosed embodiment, when the local unipolar minimum derivatives are less than a preset unipolar derivative threshold, the times of occurrence are assigned as the times of activation of the myocardium.

Typically, classifying the unipolar signal includes defining a plurality of preset classifications for the unipolar signal. The plurality may include a first classification wherein the number is zero, a second classification wherein the number is one, a third classification wherein the number is two or three, and a fourth classification wherein the number is greater than three.

In an alternative embodiment the method includes only assigning a given time of occurrence as a given time of activation of the myocardium when a confidence level associated with the given time of occurrence is greater than a preset confidence level. In some embodiments the given time of occurrence may only be assigned as the given time of activation of the myocardium when an amplitude of a corresponding bipolar signal is greater than a preset bipolar signal threshold.

There is further provided, according to an embodiment of the present invention apparatus, including:

a pair of electrodes configured to be placed in proximity to a myocardium of a human subject; and a processor configured to:

receive a bipolar signal from the pair of electrodes, receive a unipolar signal from a selected one of the pair of electrodes, delineate a window of interest (WOI) for the unipolar and bipolar signals, within the WOI compute local unipolar minimum derivatives of the unipolar signal, and times of occurrence of the local unipolar minimum derivatives, within the WOI compute bipolar derivatives of the bipolar signal at the times of occurrence, evaluate ratios of the bipolar derivatives to the local unipolar minimum derivatives, when the ratios are greater than a preset threshold ratio value, assign the times of occurrence as times of activation of the myocardium, count a number of the times of activation; and classify the unipolar signal according to the number.

The present disclosure will be more fully understood from the following detailed description of the embodiments thereof, taken together with the drawings, in which:

BRIEF DESCRIPTION OF THE DRAWINGS

FIG. 23 is a schematic illustration of an invasive medical procedure using an apparatus, according to an embodiment of the present invention.

DETAILED DESCRIPTION EMBODIMENTS

Overview

Figure 1:
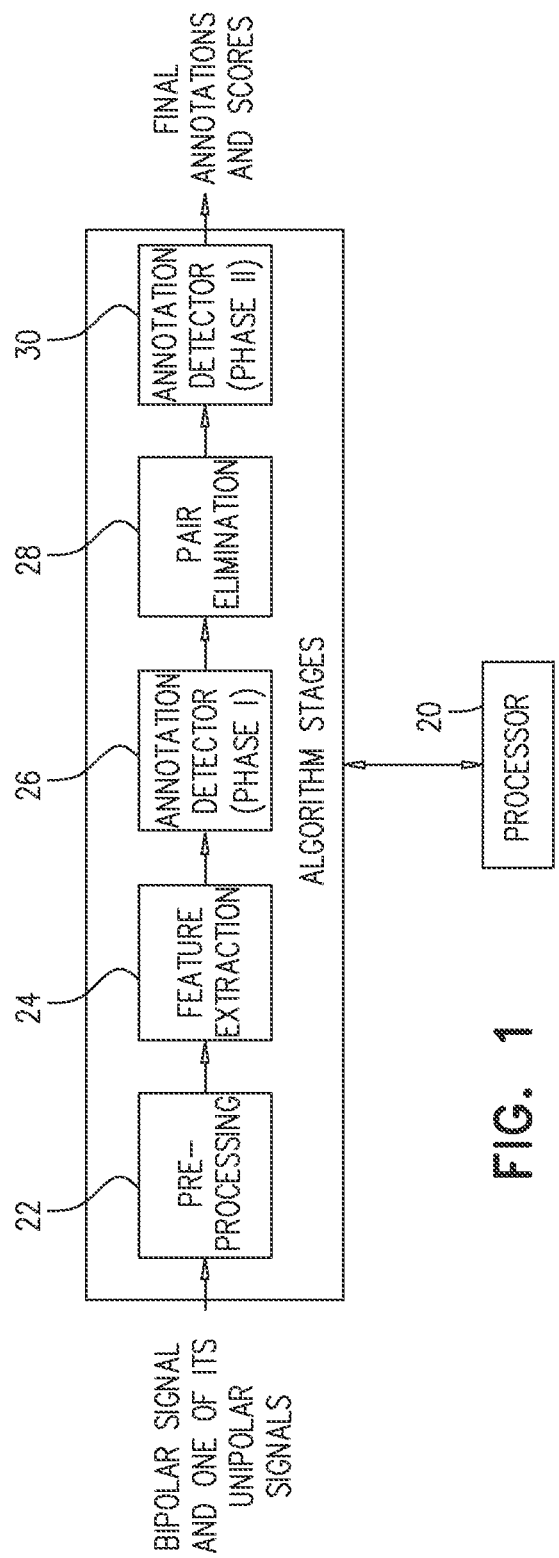
FIG. 1 is a schematic block diagram of an algorithm, according to an embodiment of the present invention.

Embodiments of the present invention use a wavefront annotation algorithm which acts to combine the properties of two types of ECG signals—a bipolar signal together with one of its associated unipolar signals—to generate accurate signal annotations. The inventors have verified that the algorithm provides accurate annotations which are immune to far field interferences.

The wavefront annotation algorithm provides automatic and reliable detection of annotation points that enable acquisition and annotation of numerous LAT points in a relatively short time. This abundance of LAT points makes it difficult and time consuming for the user to inspect each and every one of those Intra-cardiac signals for additional important clinical information that may be embedded in the signals.

Consequently, embodiments of the present invention use a classification algorithm wherein results derived from the wavefront annotation algorithm automatically identify key signals which may be of added clinical importance. Specifically, the automatic identification by the classification algorithm separates between no activation events, single activation events and multiple activation events, and within the multiple activation events separates between points with a large number of activations and those points with only a few activations.

A classification algorithm classifies ECG signals according to their complexity. This algorithm measures complexity using enumeration—by counting the number of detected valid activations within a given time window. The inputs to the algorithm are wavefront detected activations from a wavefront annotation algorithm, and a time segment (WOI) for which the complexity calculation is required. The output of the classification algorithm is the classification of an ECG signal. The algorithm classification types are No-Lat, Single, Split and Multi.

An embodiment of the present invention provides a method comprising receiving a bipolar signal from a pair of electrodes in proximity to a myocardium of a human subject, and receiving a unipolar signal from a selected one of the pair of electrodes. A window of interest (WOI) is delineated for the unipolar and bipolar signals, and within the WOI local unipolar minimum derivatives of the unipolar signal and times of occurrence of the local unipolar minimum derivatives are computed.

In addition, within the WOI bipolar derivatives of the bipolar signal at the times of occurrence are computed and ratios of the bipolar derivatives to the local unipolar minimum derivatives are evaluated. When the ratios are greater than a preset threshold ratio value, the times of occurrence are assigned as times of activation of the myocardium, a number of the times of activation is counted, and the unipolar signal is classified according to the number.

Description of Embodiments

The following description is divided into two sections. A first section describes the wavefront annotation algorithm. A second section describes the classification algorithm.

1. Wavefront Annotation Algorithm

FIG. 1 is a schematic block diagram of a wavefront annotation algorithm, according to an embodiment of the present invention. The algorithm inputs consist of a single bipolar signal and one of its unipolar signals, which are typically provided to a processor 20 operating the algorithm, following a low pass filter with a cut-off of 500 Hz and a power rejection filter. More detail of the operation of processor 20 is provided with reference to FIG. 23 below. The polarity of the unipolar signal is assumed to be known (i.e. it is derived from either a positive or a negative electrode). The processor may be a stand-alone processor, and/or a general purpose processor that is typically operating a computer. The algorithm comprises a number of stages, summarized here.

A pre-processing stage 22 includes removal of baseline wander, low pass filtering and any order of differentiation. The removal of baseline wander includes removal of an additive low frequency signal that is an artifact and originates from various reasons such as mechanical catheter movement or respiration. This low frequency signal can alter the estimated derivative of the signals and therefore is typically removed.

A feature extraction stage 24 uses the post-processed signals and extracts features for every candidate annotation.

A first annotation detector stage 26 performs eliminations of candidate annotations based on a subset of features.

Next, in a pair elimination stage 28 candidate annotations that pass the required feature threshold, but are insignificant relative to another very close activation may be discarded.

Finally, in a second annotation detector stage 30 a score is given to each candidate annotation based on its feature values. Only candidate annotations that surpass the score thresholds are considered as valid annotations, and the timing and features of these are used by the processor in further operations of the processor, such as generating a map of the candidate annotations.

The elements of the algorithm are described in more detail below.

The core of the algorithm relies on three basic observations:

Unipolar activity is marked by a sharp downward deflection in the signal amplitude. These deflections can be easily identified as local minima in the activity velocity signal (i.e. the derivative of the unipolar signal). However, not all local minima are indicative for activity; some are results of noise or far field activity. Therefore, the purpose of the algorithm is to distinguish between local minima in the velocity signal that are correlated with local real activations and those that are not. This is possible using the next observation.

Far field activations affect the potential of the unipolar pair almost identically. Therefore, their bipolar counterpart has only residual activity during far field activation. This is not the case during local activity measurements when one of the electrodes is in proximity with the activation and the other is relatively far (even a few mm is sufficient). In this case the bipolar signal will also exhibit slope change concurrent with the slope change in the unipolar signal (see FIG. 2 and its description below). Using this phenomenon it is possible to distinguish between unipolar sharp deflections arising from near field activations and those arising from far field activations.

Combining multiple features of candidate annotations provides a method for making a more robust annotation detection. For example, bipolar amplitude change as a result of local activation may be used as a feature. However, sometimes a far field activation may have a bipolar component (for example when mapping inferior atria near the ventricle valve). Therefore, decision making that is based solely on the bipolar amplitude may fail. However, if additional features of the signals are used the decision making may be more robust. One such feature can be the unipolar amplitude around the activation (FIG. 2).

Figure 2:
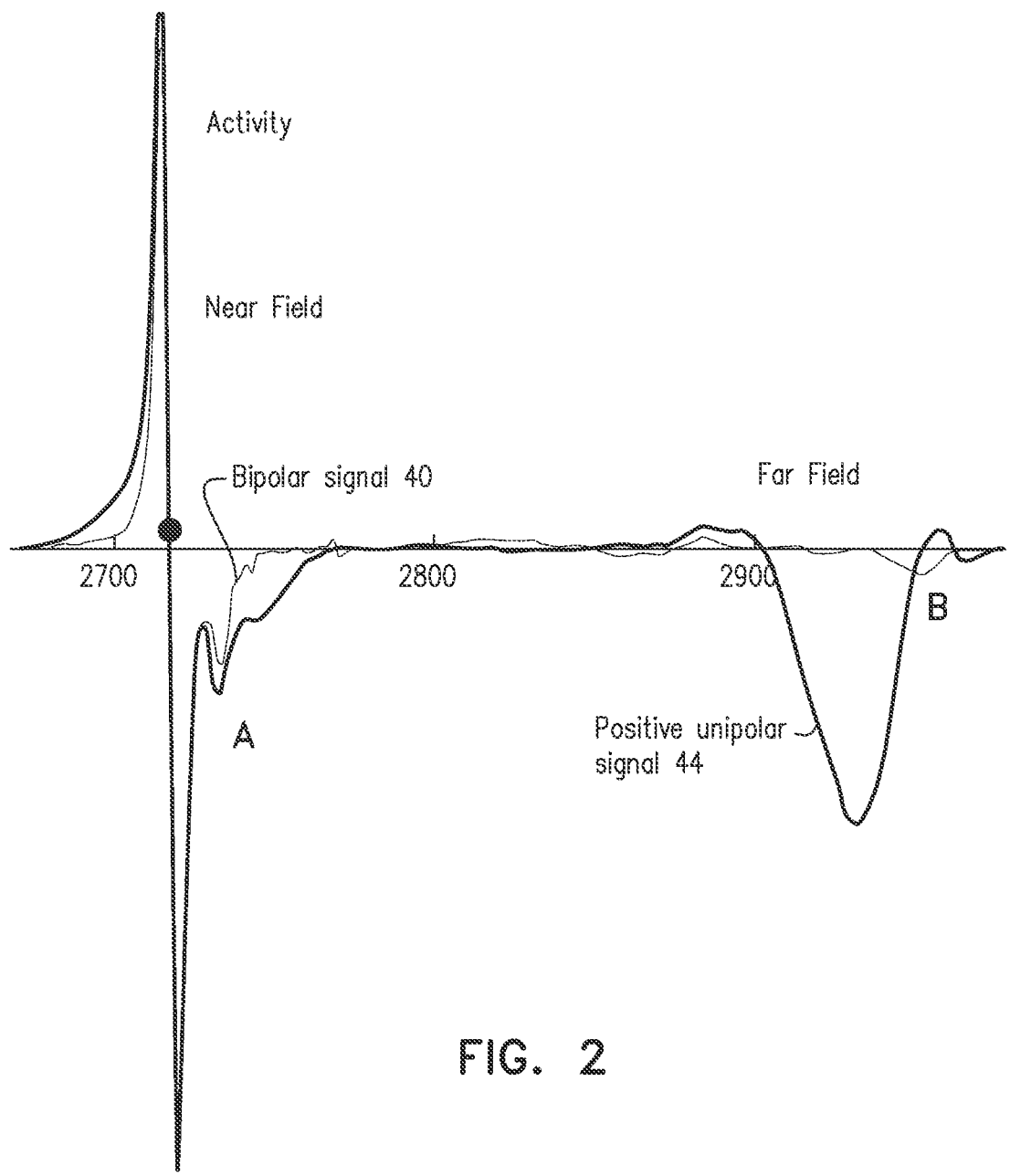
FIG. 2 is an example of activity as measured by a bipolar signal and a unipolar positive electrode signal, according to an embodiment of the present invention.

FIG. 2 is an example of activity as measured by the bipolar signal and the unipolar positive electrode signal, according to an embodiment of the present invention. A graph 40 shows the bipolar signal; a graph 44 shows the unipolar signal. The sharp downward deflection on the left, in a region "A", is a near field activity which is concurrent in the unipolar and the bipolar signals. As shown in a region "B" during far field ventricular activation the unipolar signal changes, however, the bipolar activity is negligible. Embodiments of the present invention use multiple features of the signal similar to those exemplified above to assist in separating between local and far field activations. For example, in region A the unipolar amplitude and its rate are similar to the bipolar signal, while in region B the unipolar signal amplitude is much larger and its rate is much faster than the bipolar signal.

The following description describes the elements of the algorithm illustrated in FIG. 1.

Pre-Processing and Feature Extraction Stages 22 and 24 (FIG. 1)

The purpose of these pre-processing and feature extraction stages is to remove and attenuate interferences in the unipolar and bipolar signals while maintaining and emphasizing those features of the signal that are used in subsequent stages. While for simplicity the actions described herein are assumed to occur in stages 22 and 24, it will be understood that at least some of these actions may occur in other stages of the algorithm. A characteristic that we want to retain is the morphology of activations, since it reflects slope changes. Characteristics that are typically discarded are the baseline wander that acts as an additive signal that can corrupt the slope measurements and also high frequency noise. Stages 22 and 24 are divided into four sub-stages:

1. Unipolar Pre-Processing Sub-Stage

The Unipolar pre-processing stage consists of applying the following steps in series:
1. Baseline estimation and subtraction (using a median filter+a low pass filter (LPF)) at 1 KHz
2. Upsampling to 8 KHz (Sample and hold or other upsampling technique by factor of 8)
3. First Smoothing Filter—LPF FIR (−6 db@155 Hz, 145 Taps). The filter is a convolution of a 65 taps Equiripple filter of 500 Hz and Gaussian 10 ms window.
4. Second Smoothing Filter—The filter used is an antialiasing LPF of the system, typically a 500 Hz low pass filter.
5. Derivative The derivative of step 5 is used as an input to a unipolar annotation detector-(Phase I) in first annotation detector stage 26 (FIG. 1). The additional filtered signal output of step 4 is used for feature extraction stage 24 of the algorithm.

2. Bipolar Pre-Processing Sub-Stage

The bipolar pre-processing stage consists of applying the following steps in series:
1. Baseline estimation and subtraction (median filter+LPF) at 1 KHz
2. Upsampling to 8 KHz (Sample and hold by factor of 8)
3. Smoothing—LPF FIR (−6 db@310 Hz, 113 Taps). The filter is a convolution of a 65 taps Equiripple filter of 500 Hz and Gaussian 6 ms window.
4. Derivative The final output of the bipolar preprocessing stage (the bipolar derivative) is used as an input to the unipolar annotation detector-(Phase I) referred to above (FIG. 1).

3. Baseline Wander Estimation Sub-Stage

Intra-cardiac (IC) signals may contain additive baseline wander signals arising from movement of the catheter, movement of the subject and respiration that changes the interface with the tissue (see FIG. 3 and its description below). These motion artifacts contain mostly low frequency components. However, the near field activity signal may also contain significant energy in these spectral bands. Therefore the conventional approach of removal by high pass IIR or FIR filter is problematic and can cause distortion and morphology changes to the IC signals. Consequently, the selected approach that we use is based on estimation of the baseline wander (FIG. 3) and its subtraction from the signal.

Figure 3:
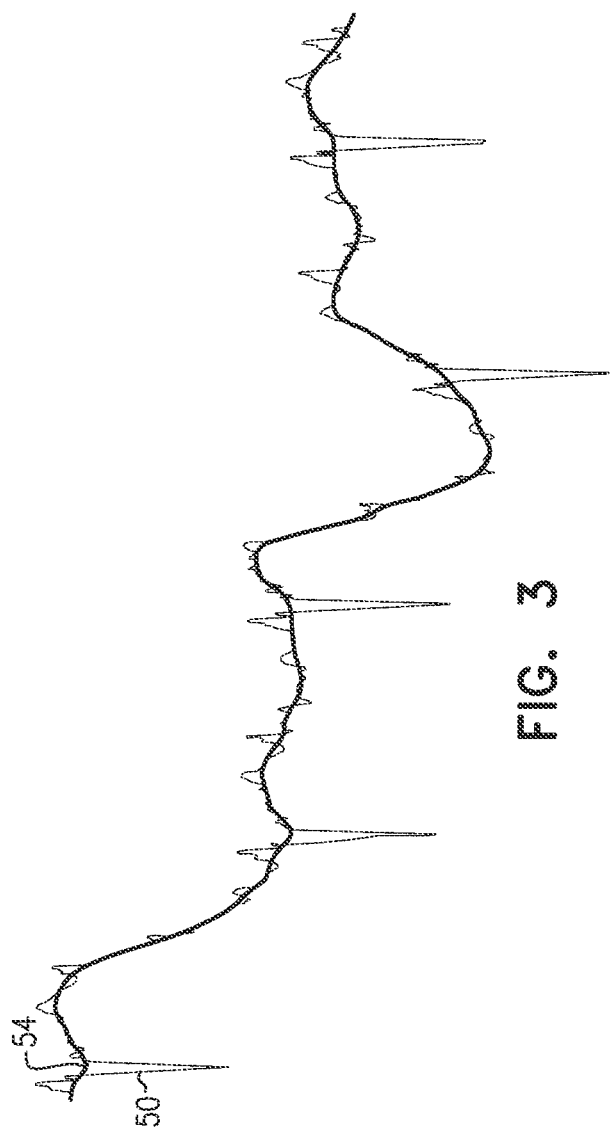
FIG. 3 is a graph illustrating baseline wander removal, according to an embodiment of the present invention.

FIG. 3 is a graph illustrating baseline wander removal, according to an embodiment of the present invention. A unipolar signal 50 is originally contaminated by a low frequency artifact, contributing to the baseline wander. The purpose of the baseline estimation is to calculate the baseline which is then subtracted from the signal. In the figure a calculated baseline 54 has been overlaid on the unipolar signal. Baseline wander rejection is important since baseline wander can add noise to the estimate of the unipolar derivatives, and thus may affect the annotation detection.

Figure 4:
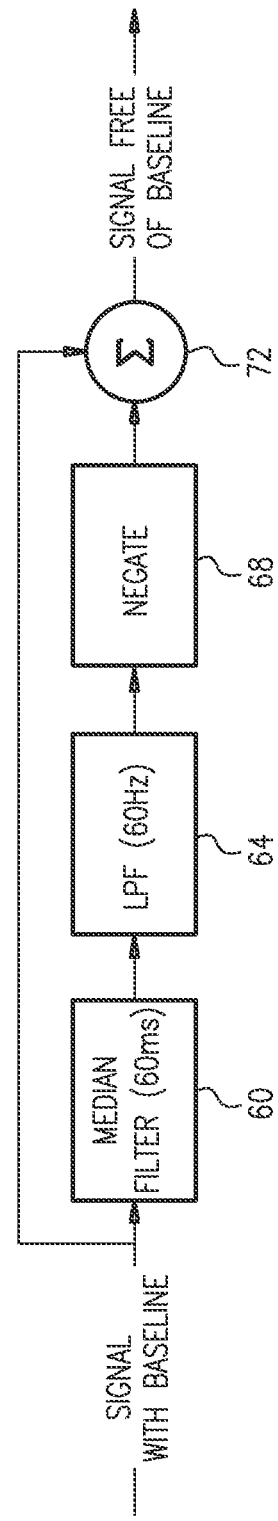
FIG. 4 is a block diagram of a baseline wander removal system, according to an embodiment of the present invention.

The estimation of the baseline wander, and its subtraction from the original, is accomplished by removal of the near field activity using a series of two filters as is illustrated in FIG. 4.

FIG. 4 is a block diagram of a baseline wander removal system, according to an embodiment of the present invention. A median filter 60, typically having a window of 60 ms, is designed to remove the activities from the raw signal while an LPF 64, which in one embodiment is an 89 taps FIR Hanning filter with a typical cut-off of approximately 10 Hz, is designed to smooth out edges resulting from the median filter. Finally the baseline estimate is subtracted from the raw signal, by a process of negation 68 then summation 72, resulting in a signal free of baseline wander.

4. Smoothed Derivative Sub-Stage

Figure 5:
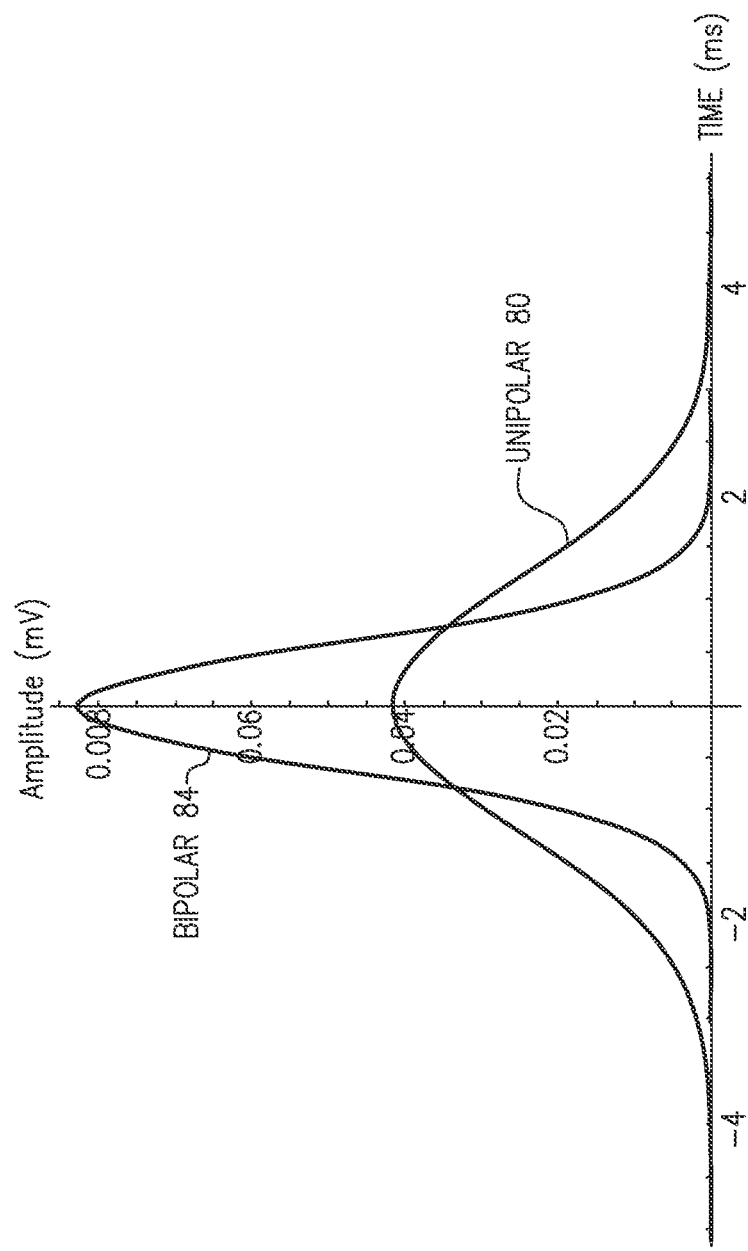
FIG. 5 is a graph of two Gaussian filters, according to an embodiment of the present invention.

FIG. 5 is a graph of two Gaussian filters, according to an embodiment of the present invention. The detection of sharp deflection points in the signal is based on the velocity of the signal, therefore a derivative approach is used. However, derivative functions act as a high pass filter, thus enhancing high frequency noise. Therefore, we use a smoothing function to decrease the noise in the derivative estimation. The smoothing function that we use are normalized zero mean Gaussian functions, comprising a unipolar Gaussian function 80 and a bipolar Gaussian function 84, illustrated in FIG. 5. These unipolar and bipolar Gaussian filters have 90% of the energy in time windows of ±2 ms and ±1 ms respectively. Thus activations or approaching far fields at distances larger than these values are virtually ignored and do not affect the derivative value.

Annotation Detector-I Stage 26 (FIG. 1)

Figure 6:
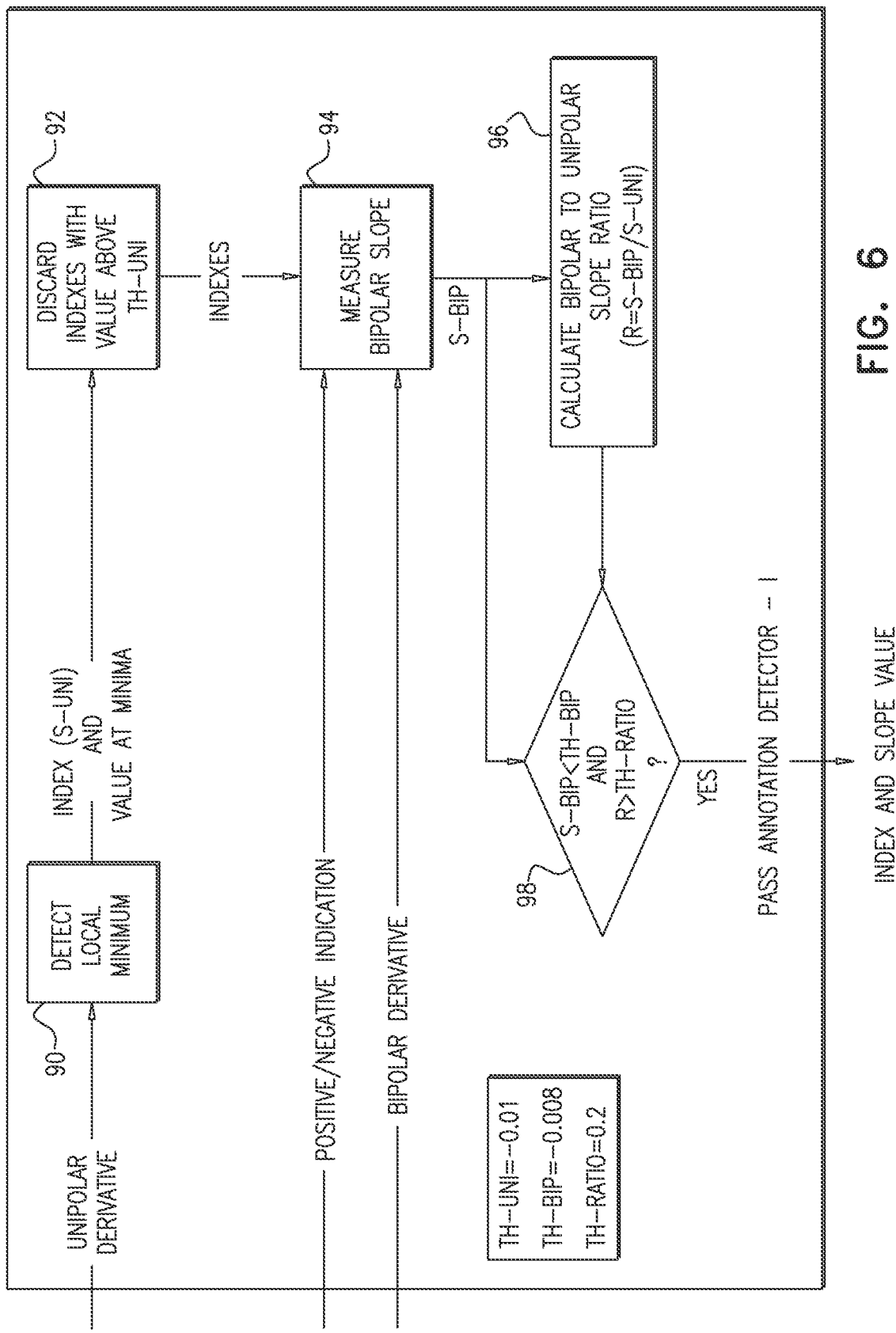
FIG. 6 is a schematic block diagram of an Annotation Detector block according to an embodiment of the present invention.
Figure 7:
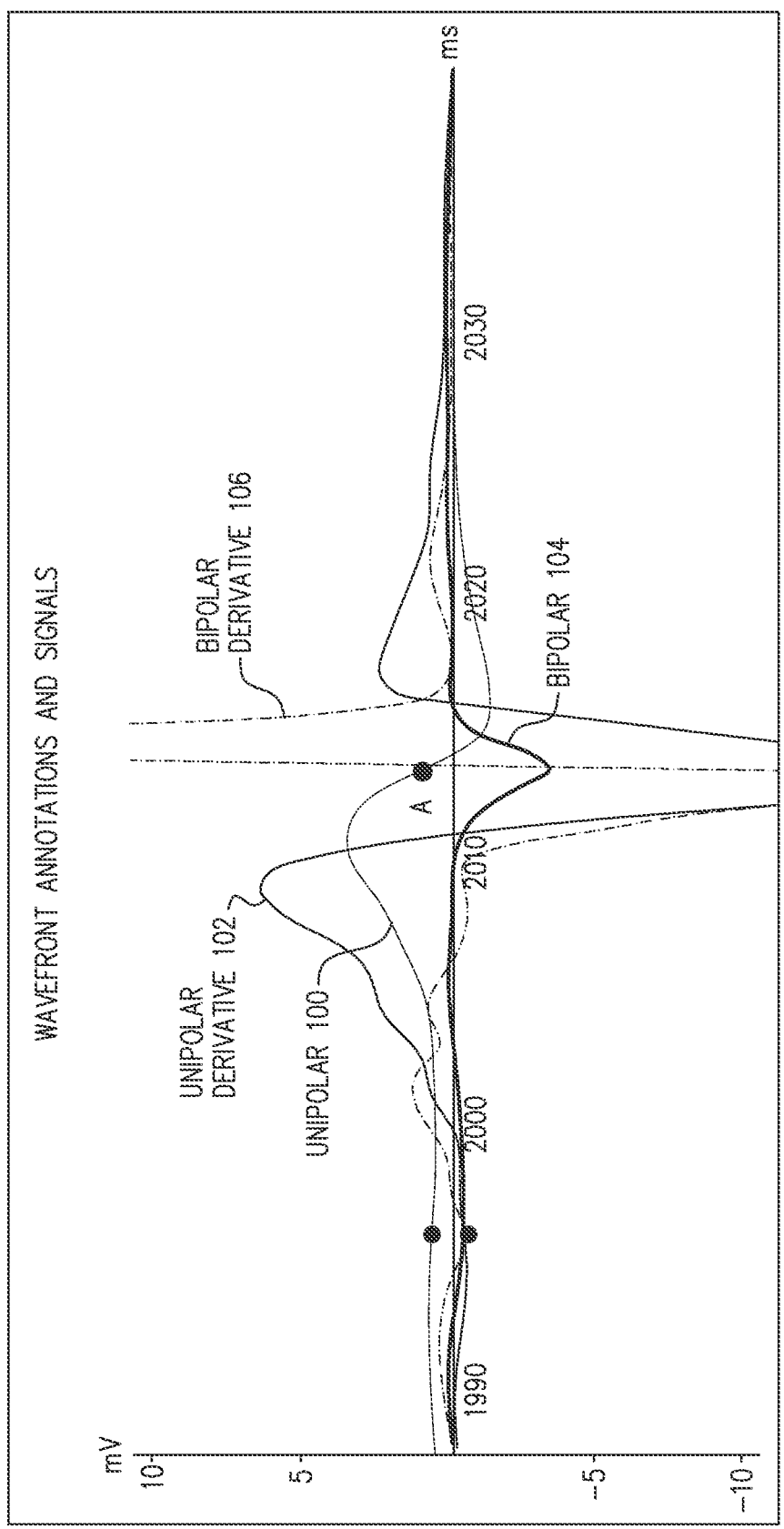
FIG. 7 is a graph of unipolar and bipolar signals, and their derivatives, according to an embodiment of the present invention.
Figure 8:
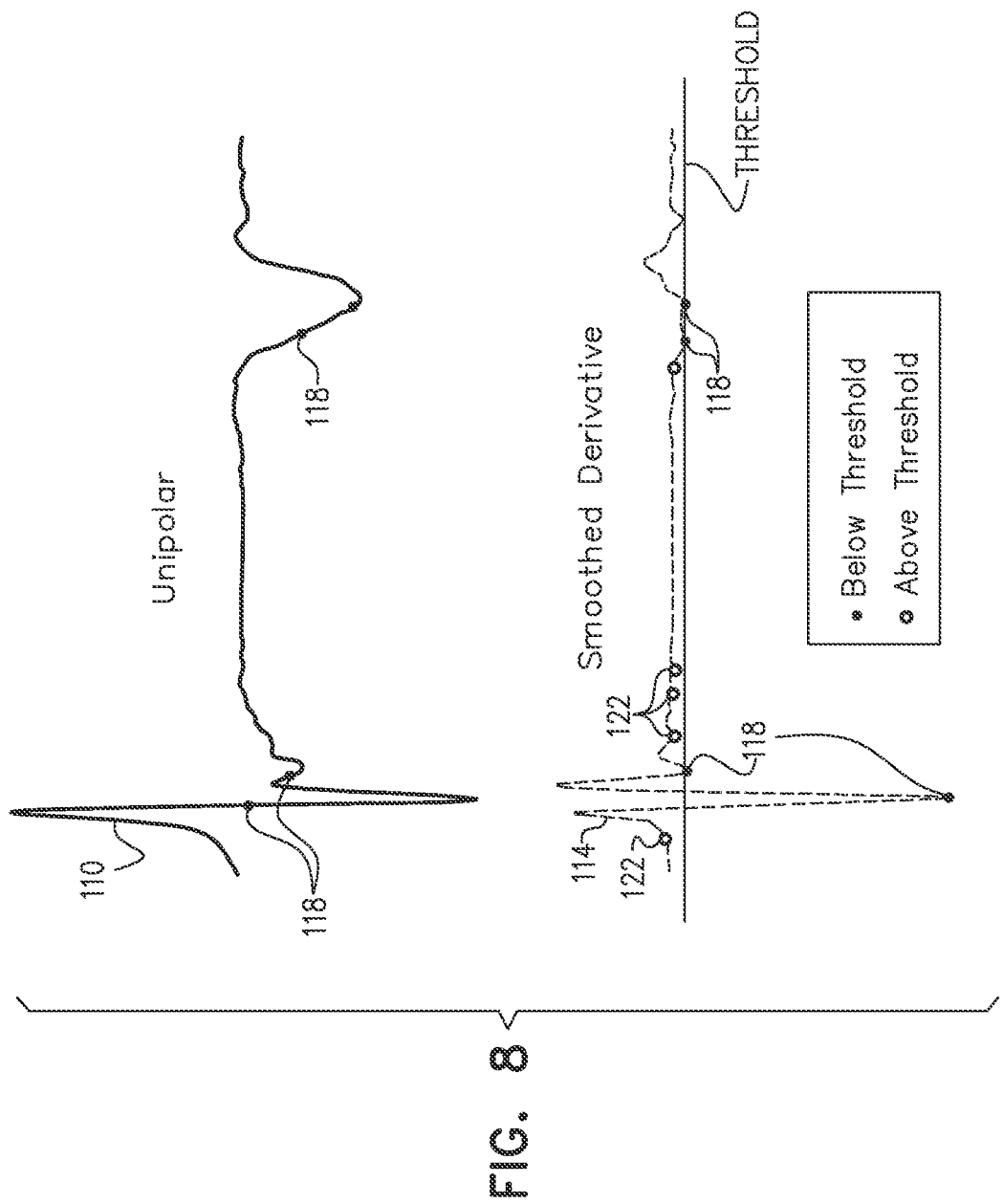
FIG. 8 shows graphs illustrating a first rejection phase of an annotation algorithm, according to an embodiment of the present invention.

Reference is now made to FIGS. 6-9. FIG. 6 is a schematic block diagram of Annotation Detector-I stage 26; FIG. 7 is a graph of unipolar and bipolar signals, and their derivatives; FIG. 8 has graphs illustrating a first rejection phase of the annotation algorithm; and FIG. 9 has graphs illustrating local and far field candidate annotations, according to embodiments of the present invention.

Referring to FIG. 6, Table I below gives parameters used in the detector, and corresponding acronyms in the block diagram.

TABLE I

| Parameter | Acronym |
| --- | --- |
| Smoothed Unipolar Derivative | S-Uni |
| Smoothed Unipolar Derivative Threshold | Th-Uni |
| Smoothed Bipolar Derivative | S-Bip |
| Smoothed Bipolar Derivative Threshold | Th-Bip |
| $\frac{S-Bip}{S-Uni}$ | R |
| The minimal ratio that R should exceed in order to be a valid annotation at the output of annotation detector-I | Th-Ratio |

FIG. 7 shows an example of a bipolar slope of zero around a unipolar annotation. The graphs show a unipolar distal signal 100, its derivative 102, its local activation (A) as well as a bipolar signal 104, and its derivative 106. Notice that at the unipolar deflection point (A) the bipolar derivative is almost zero and it is not indicative of the large change in bipolar amplitude.

FIG. 8 has graphs illustrating a first rejection stage of the annotation algorithm of FIG. 1. A top graph 110 shows the unipolar signal and a bottom graph 114 shows its smoothed derivative. Black dots 118 are minima values in the derivative signal below a threshold value and will be further considered as possible annotation points while grey dots 122 mark minima value above the threshold that will be rejected.

Figure 9:
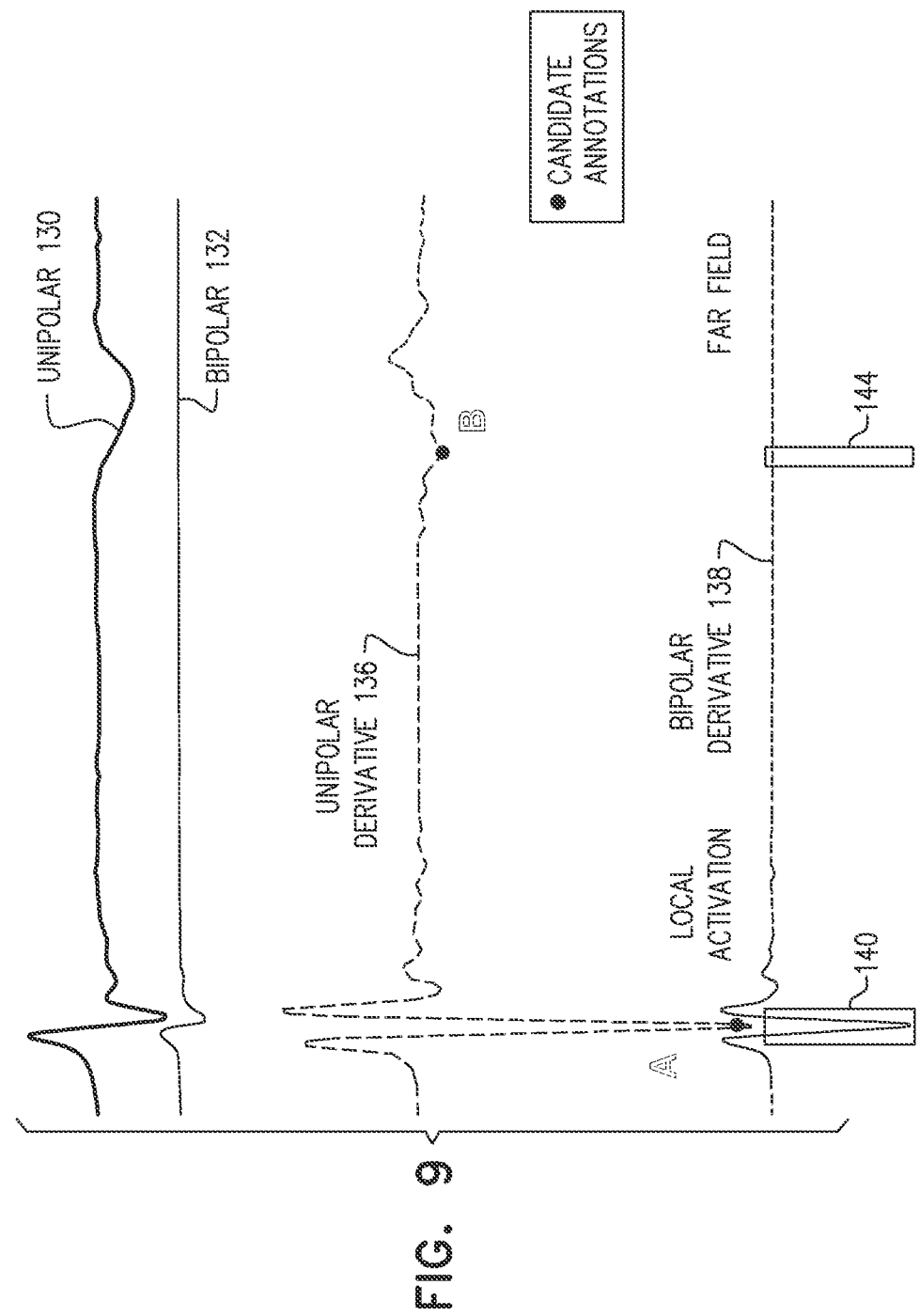
FIG. 9 shows graphs illustrating local and far field candidate annotations, according to an embodiment of the present invention.

FIG. 9 illustrates separation between local (A) and far field (B) candidate annotations using the bipolar and unipolar derivative ratio feature described herein. The figure shows unipolar 130 and bipolar 132 signals, and unipolar 136 and bipolar 138 derivatives. In local activation, unipolar derivative changes are accompanied by a bipolar derivative change as illustrated by a 2 ms activity window 140. However, this is not the case in the far field derived deflection (B), as illustrated by window 144, thus the ratio between the change in the bipolar and unipolar slope for the far field case will be below the required ratio threshold.

Returning to FIG. 6, the inputs for the annotation detector-I block are the relevant unipolar signal derivative under test, its polarity and its smoothed bipolar derivative. The outputs of the block are the annotation indexes and their slope value (the unipolar derivative value at the annotation index). The slope value acts as the score of the annotation.

In an embodiment of the invention the deflection points in the downslopes of the unipolar signal are detected, in blocks 90 and 92, by finding the minima points below a threshold (typically −0.01 mv/ms), see also FIG. 8. Activities typically satisfy this condition in addition to two others:

1. The value of the bipolar smoothed derivative signal (S-BIP) in a time window around the unipolar deflection points (typically ±2 ms) should exceed in a negative manner, a threshold TH-BIP. Thus, S-BIP<TH-BIP. In one embodiment TH-BIP is typically about 0.008 mv/ms.
2. The ratio between this bipolar smoothed derivative value and the unipolar smoothed derivative slope value should be higher than Th-Ratio, typically about 0.2.

1 and #2 are evaluated in blocks 94 and 96, and in a decision 98.

Referring to FIG. 6, the bipolar derivative value (S-bip) is computed differently for positive and negative electrodes. In a disclosed embodiment, for a positive electrode it is the minimal value within a 2 ms time window, and for a negative electrode it is the negative value of the maximal value within that time window. The reason for using a time window and not the derivative at the annotation point is that in certain pathologies and/or orientations (of the catheter and the wave propagation direction) the bipolar signal at a given point can be small or even zero since the time delay of activities between unipolar activations can cancel out (FIG. 7). The value is calculated differently for positive and negative electrodes since the tip activity at the positive electrode is registered as a downslope in the bipolar signal, while activity at the negative electrode is registered as an upslope in the bipolar signal.

The ratio between the unipolar and the bipolar derivatives may also be used as a classification criterion since this criterion can distinguish between near field and far field activity. In near field activity at least some of the downslope activity is typically represented in the bipolar signal, while in far field cases the bipolar signal may only have residual activity.

Pair Elimination Stage 28 (FIG. 1)

The pair elimination stage of the algorithm is responsible for merging two annotations that arise from a single activity. This split phenomena can occur when for some reason the downward slope of a near field activity contains a momentary upslope, either from activity recorded in the other electrode or from far field activity that influences one electrode more than the other. The momentary upslope will cause two minima in the derivative of the signal, and if these are strong enough they result in two annotations. In order to exclude these cases we evaluate the change in the signal due to the upslope.

All annotation pairs in the same unipolar signal that are not too far apart (typically less than 50 ms) are analyzed for a split. The segment between the two candidate annotations in the unipolar derivative signal is analyzed for upsloping. When the upsloping amplitude is considered significant the two annotations are maintained. If not, the annotation with a smaller downslope is discarded.

Figure 10:
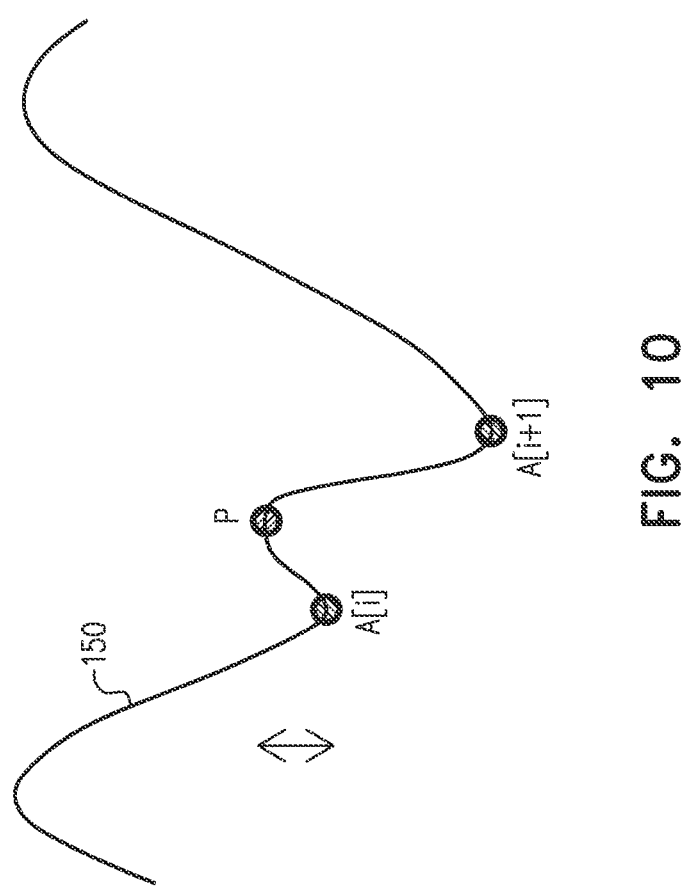
FIG. 10 is a graph illustrating merging of candidate annotations, and how rejection criteria are used, according to an embodiment of the present invention.

FIG. 10 is a graph 150 illustrating merging of candidate annotations, and how rejection criteria are used, according to an embodiment of the present invention. The graph shows a unipolar derivative signal and two possible annotations (circles, marked A[i] and A[i+1]).

The purpose of pair elimination block 38 is to decide whether the upsloping amplitude change (marked with a vertical double-headed arrow) between the smallest derivative amplitude and the peak P between the two possible annotations is significant or not. If the change is considered significant both annotations are maintained, otherwise the weaker activation—A[i] is discarded.

Thus, for an annotation A[i] to be discarded the relative change to the peak amplitude (P) between any adjacent candidates annotation with a stronger slope within will not be rejected. In the 50 ms time windows A[i+1] is considered. If the peak is significantly higher this point mathematical terms, in one embodiment, if the value of (P−A[i])/(0.02−A[i]) is lower than 0.5 the annotation A[i] is discarded. I.e., annotation A[i] is rejected if one or more annotations in the 50 ms time window follow the above rule.

Annotation Detector II Stage 30 (FIG. 1)

The candidate annotations that passed the earlier phases are revaluated in this block using additional features and metrics. Only annotations that pass this block and that also pass a user bipolar voltage controlled threshold are considered valid annotations. For each annotation multiple features are computed. Each feature value is given a fuzzy score ranging from zero to one, corresponding to a confidence value for the feature. Finally, all scores are combined together and their value is tested against a global score threshold. Those annotations that pass the global score threshold, i.e., that have a high confidence value, are considered valid annotations and those that do not, i.e., that have a low confidence value, are rejected.

The fuzzy functions described herein are examples of such functions that are used in one embodiment of the present invention. However, other such fuzzy functions or other probabilistic terms/functions will be apparent to those having ordinary skill in the art, and all such functions are assumed to be included within the scope of the present invention. In addition, for a specific requirement multiple fuzzy scores may be used (for example—fuzzy functions that highlight strong or small bipolar signals etc.)

All fuzzy functions are bounded between 0 and 1.

The features that the block uses are:
1. The unipolar derivative value
2. The duration, $s_2$, of the unipolar slope
3. The amplitude of the unipolar slope at that time window, $s_2$
4. The ratio between the above duration and amplitude
5. The bipolar signal amplitude in the time window—$s_2$ The five features are explained below.

1. Unipolar Derivative

Figure 11:
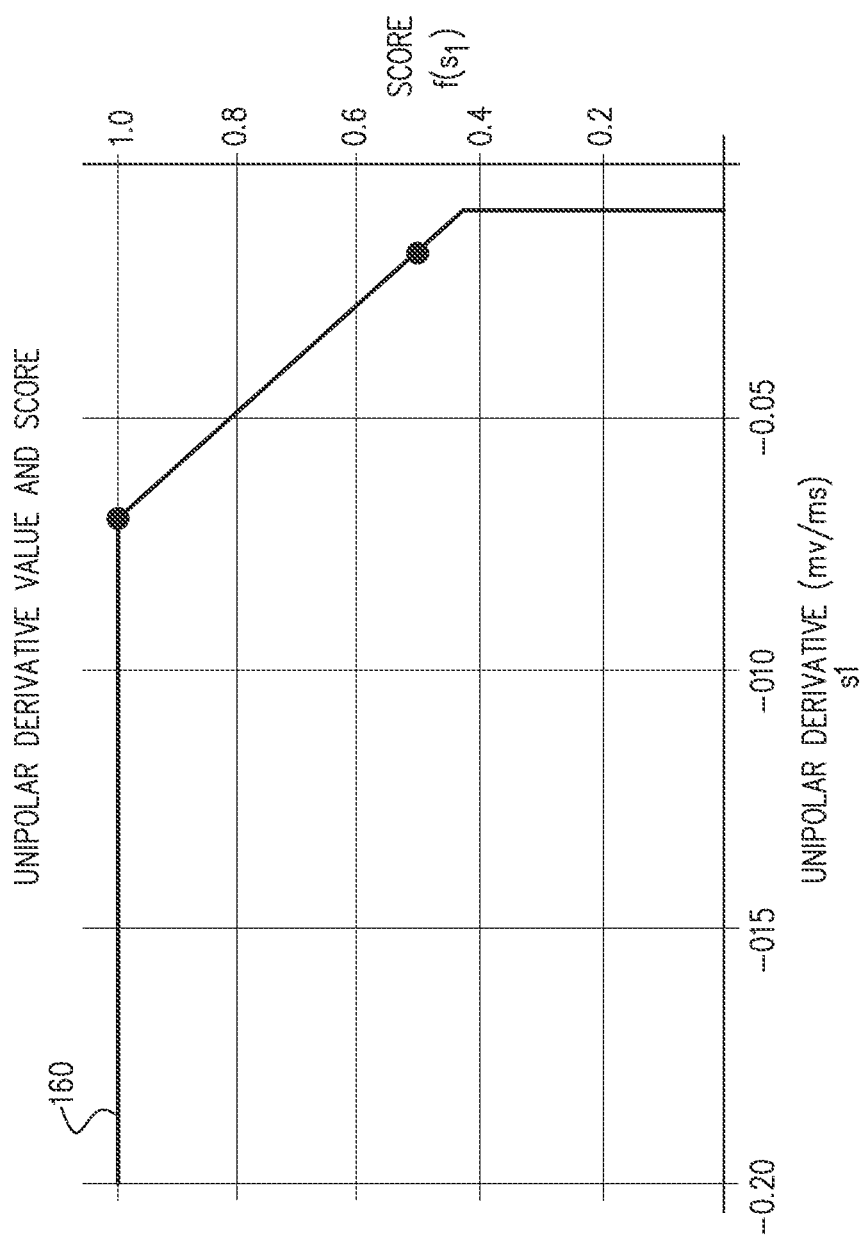
FIG. 11 is a graph of a unipolar derivative fuzzy function, according to an embodiment of the present invention.

FIG. 11 is a graph 160 of a unipolar derivative fuzzy function, according to an embodiment of the present invention. The graph provides a score $f(s_1)$ assigned to the derivative, where the derivative value is herein termed $s_1$. As shown in the graph, values of the derivative below −0.07 receive a score of 1, and values larger than −0.07 decrease linearly such that a 0.5 score is reached at a slope of −0.018. Derivative values smaller than −0.01 receive a score of zero.

The unipolar derivative $s_1$ is used in both detector stages, but unlike the first stage where it has a dichotomy threshold of 0.01 mv/ms, here its value is used to provide the score $f(s_1)$. The higher the score the more probable that this is a valid annotation according to this feature alone.

2. Unipolar Activity Segmentation and Duration

Figure 12:
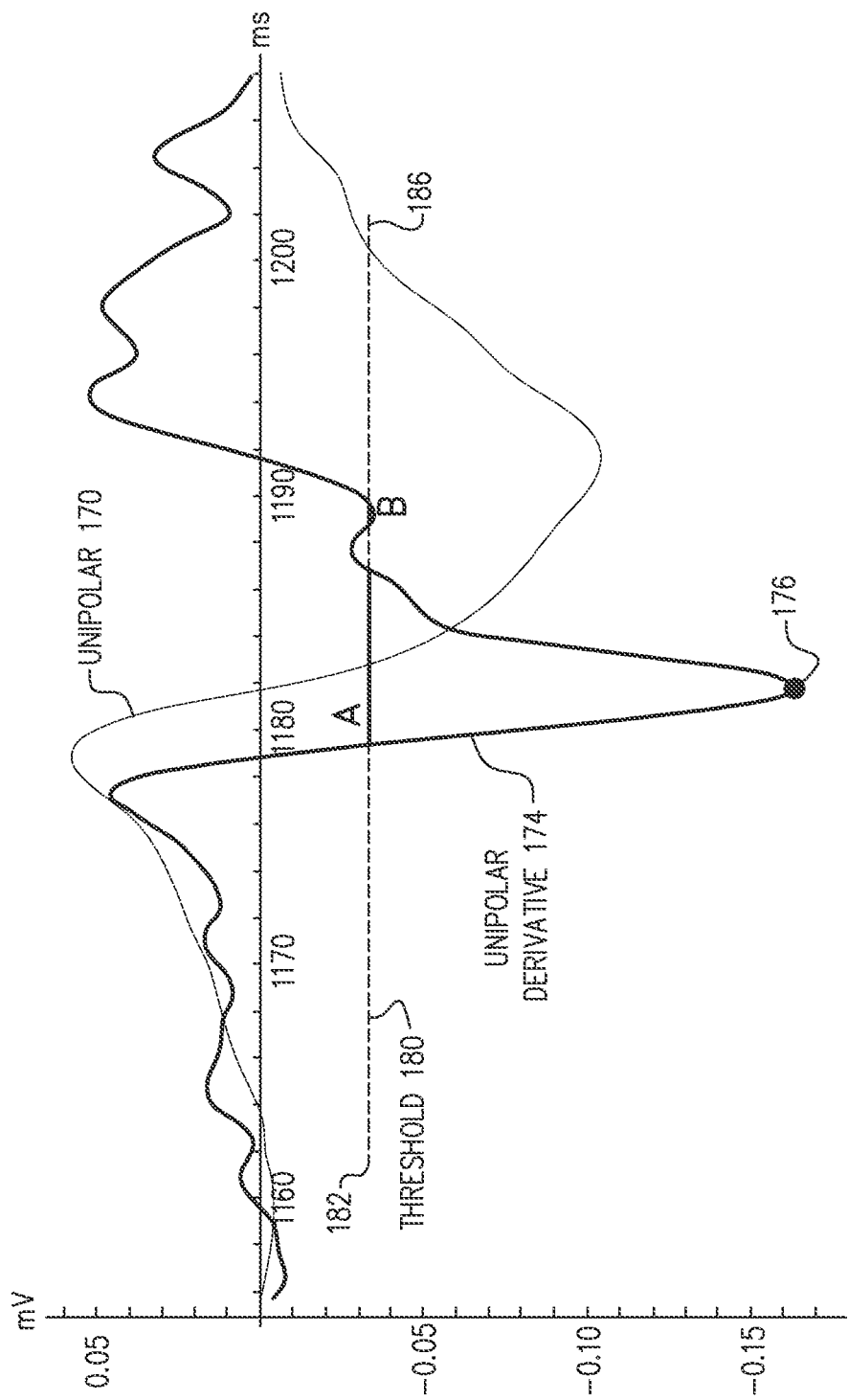
FIG. 12 is a graph illustrating unipolar signal segmentation, according to an embodiment of the present invention.

FIG. 12 shows graphs illustrating unipolar signal segmentation, according to an embodiment of the present invention. The segmentation is described further below. A unipolar signal 170 and its derivative 174 are illustrated around a candidate annotation time index 176 (black dot). A dotted horizontal line 180 representing a threshold marks a search segment (typically approximately ±25 ms) in both directions. In one embodiment the segment value is defined as 20% of the absolute maximum unipolar derivative value at the annotation point. Segments A, B mark the time intervals within the search window where the signal derivative is below the threshold. A final segment in this example can be either segment A or, if certain conditions (described hereinbelow) are met, it can be the joint segment starting from onset of A to the end of B.

A feature that we derive from the unipolar signal is the duration $s_2$ of the downslope segment around the candidate annotation. The aim is to detect the unipolar downslope from its initial descent until it starts to upslope. The motivation is to inspect features of the signals in that segment, such as properties of duration, amplitude, and their relationship, and to use them as a basis for a classifier. The inventors considered several methods for this task, all of which worked well for the obvious cases of a single slope, but the method described herein was selected since it works well on complicated cases having slope trend changes and local peaks within the slope segment.

Referring to FIG. 12, the segmentation is based on analyzing the unipolar derivative via the following steps:
1. A 50 ms segment of unipolar signal derivative 174 centered on the candidate annotation time index 176 is considered as the maximum span on threshold line 180 for which the segment can be defined. In FIG. 12 the span is between end points 182 and 186 of line 180. We assume that the unipolar signal down slope segment is bounded in this 50 ms time window. If the segment is larger than this it is force-bounded to this 50 ms interval.
2. The derivative segment amplitude is compared against a constant threshold. The threshold in the embodiment described herein is assumed to be 20% of the unipolar derivative value at the candidate annotation time. Segments on line 180 that are below that value are marked in FIG. 12 as two segments A and B.
3. The next step is to compute the segment bounds and to sum the area under the derivative at each sub-segment separately, corresponding to summing the absolute value of the signal in those segments.
4. Segments merge—Based on the segments interspacing and their area a decision is taken whether the final segment should contain the main segment (A) or additional segments (B). In one embodiment, in order for segments to join adjacent endpoints must be 1 ms or less from each other and the additional segment (B) should have an area less than 30% of the main segment, so that the signal delta for B should be less than 30% of the signal delta for A.

The duration determined from the above steps, herein termed $s_2$, is then assigned a score $f(s_2)$ using the fuzzy function described below with reference to FIG. 13.

Figure 13:
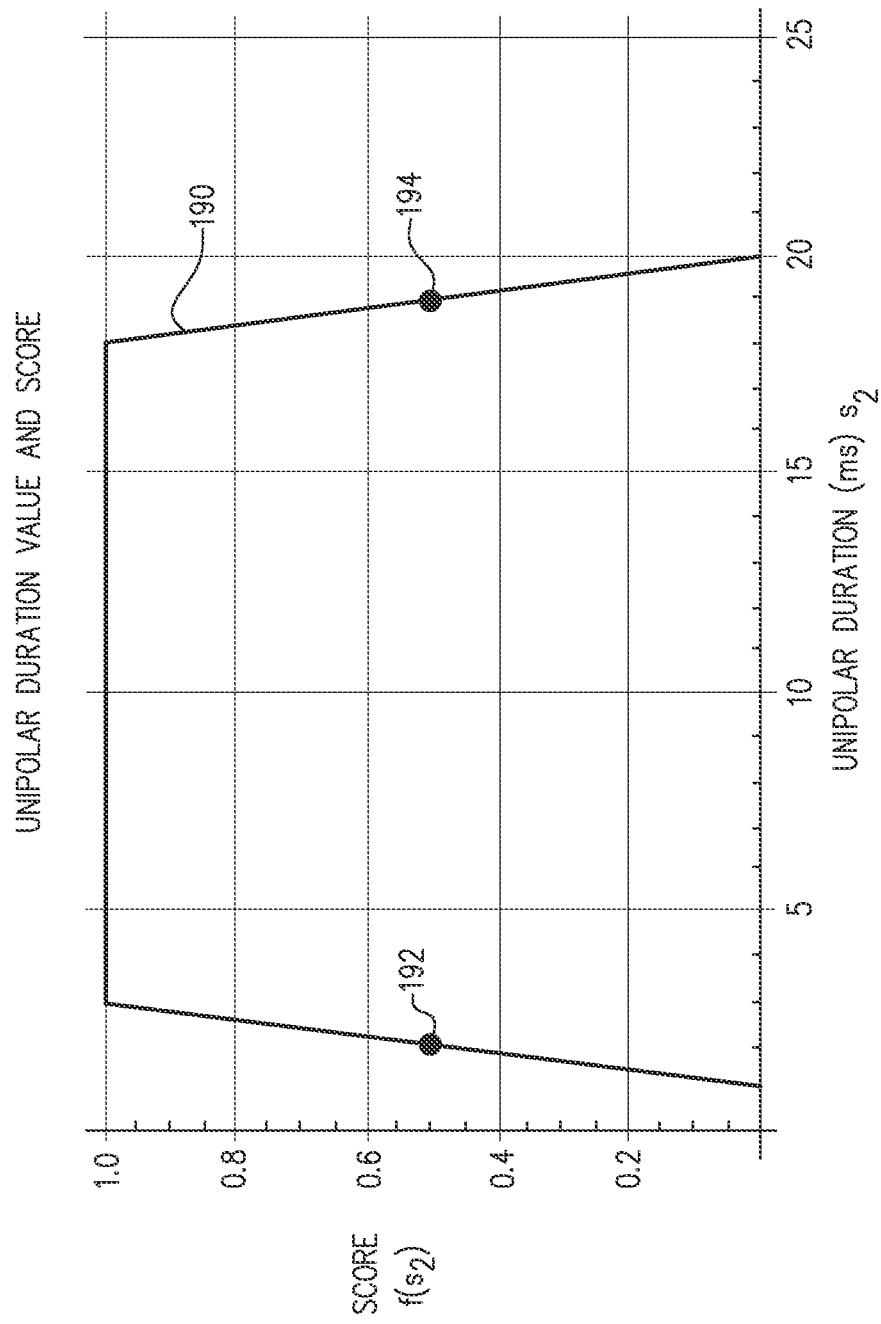
FIG. 13 is a graph of a unipolar duration fuzzy function, according to an embodiment of the present invention.

FIG. 13 is a graph 190 of a unipolar duration fuzzy function, according to an embodiment of the present invention. Very short slopes of less than 2 ms are unlikely to originate from real activation; very long activations are probably far field events. In addition, the unipolar duration for local valid activation cannot be too short and cannot be too long. The above observations are encapsulated in the fuzzy function of FIG. 13, which provides the score f($s_2$). The function points 192, 194 are: {2,0.5}.{19,0.5} and the slopes are 0.5 and −0.5 respectively.

3. Unipolar Amplitude

Figure 14:
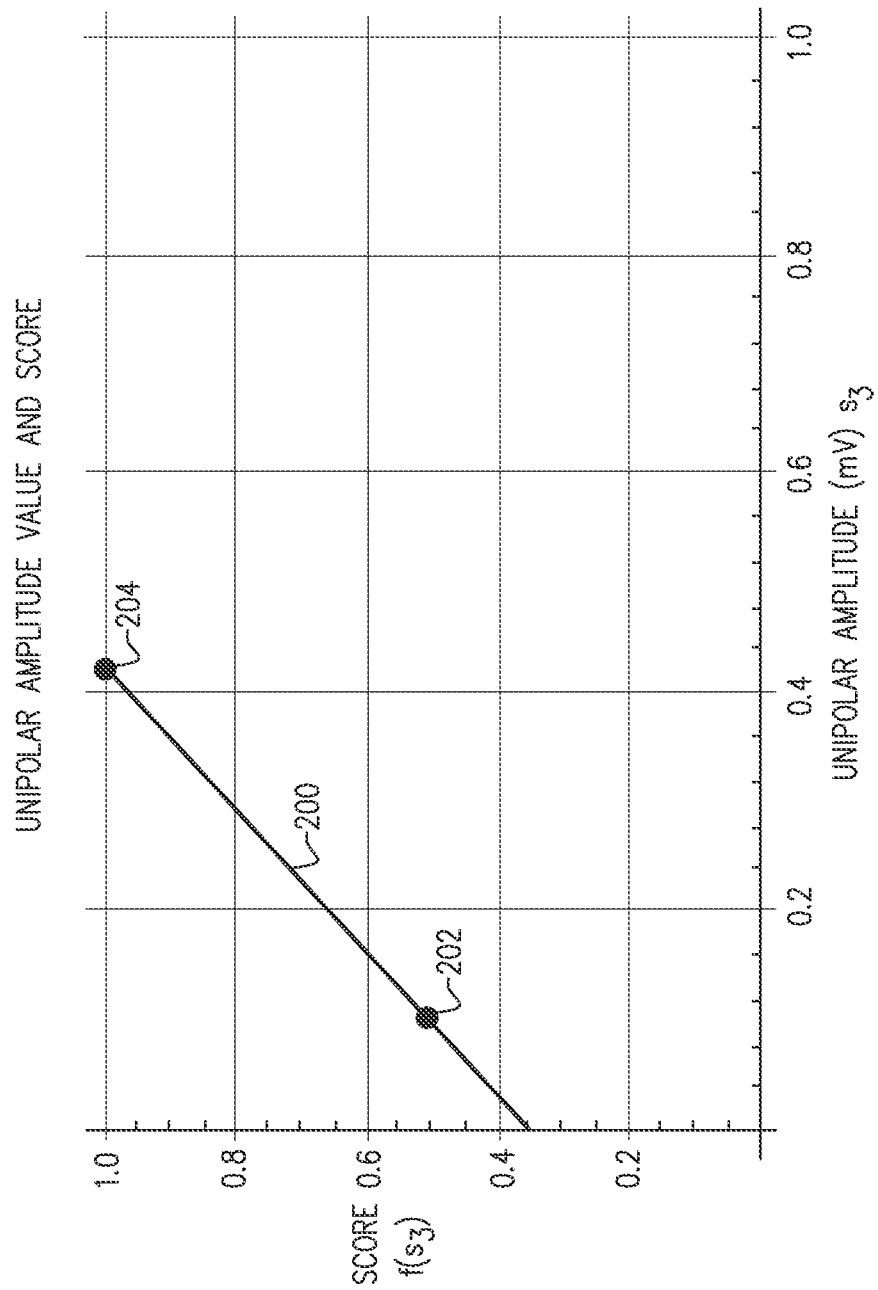
FIG. 14 is a graph of a unipolar amplitude fuzzy function, according to an embodiment of the present invention.

FIG. 14 is a graph 200 of a unipolar amplitude fuzzy function, according to an embodiment of the present invention. The unipolar amplitude is the amplitude of the unipolar signal (herein termed $s_3$) in the detected activity segment (peak-to-peak) duration $s_2$. In one embodiment the fuzzy function slope intersects points 202, 204: {0.1,0.5},{0.42, 1}. The score derived from the fuzzy function, f($s_3$), is high the higher the amplitude of the signal. I.e., for high scores, and high amplitudes, the more likely it is that the signal originates from a local activation, unless the far field signals have a large amplitude.

4. Unipolar Duration to Amplitude Ratio

Figure 15:
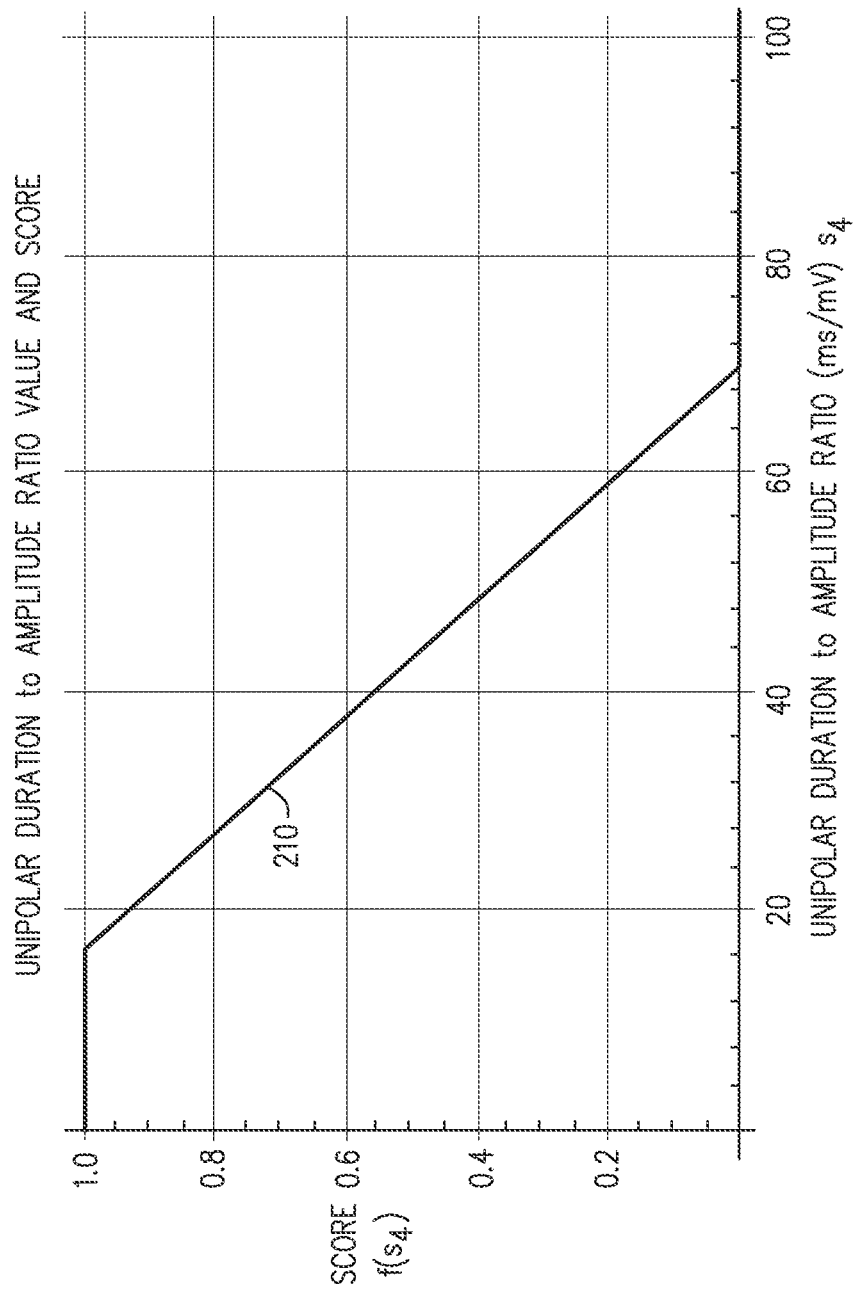
FIG. 15 is a graph of a unipolar duration to amplitude ratio fuzzy function, according to an embodiment of the present invention.

FIG. 15 is a graph 210 of a unipolar duration to amplitude ratio fuzzy function, according to an embodiment of the present invention. The unipolar duration to amplitude ratio excludes high ratio values since the longer the activity and the smaller the amplitude, the more likely that this is a false annotation. In one embodiment the equation of the fuzzy function line is $$f(s_4) = -0.0184 \cdot s_4 + 1.283 \quad (1)$$

where $s_4$ is the duration to amplitude ratio, and f($s_4$) is the score assigned to the ratio.

5. Bipolar Amplitude

Figure 16:
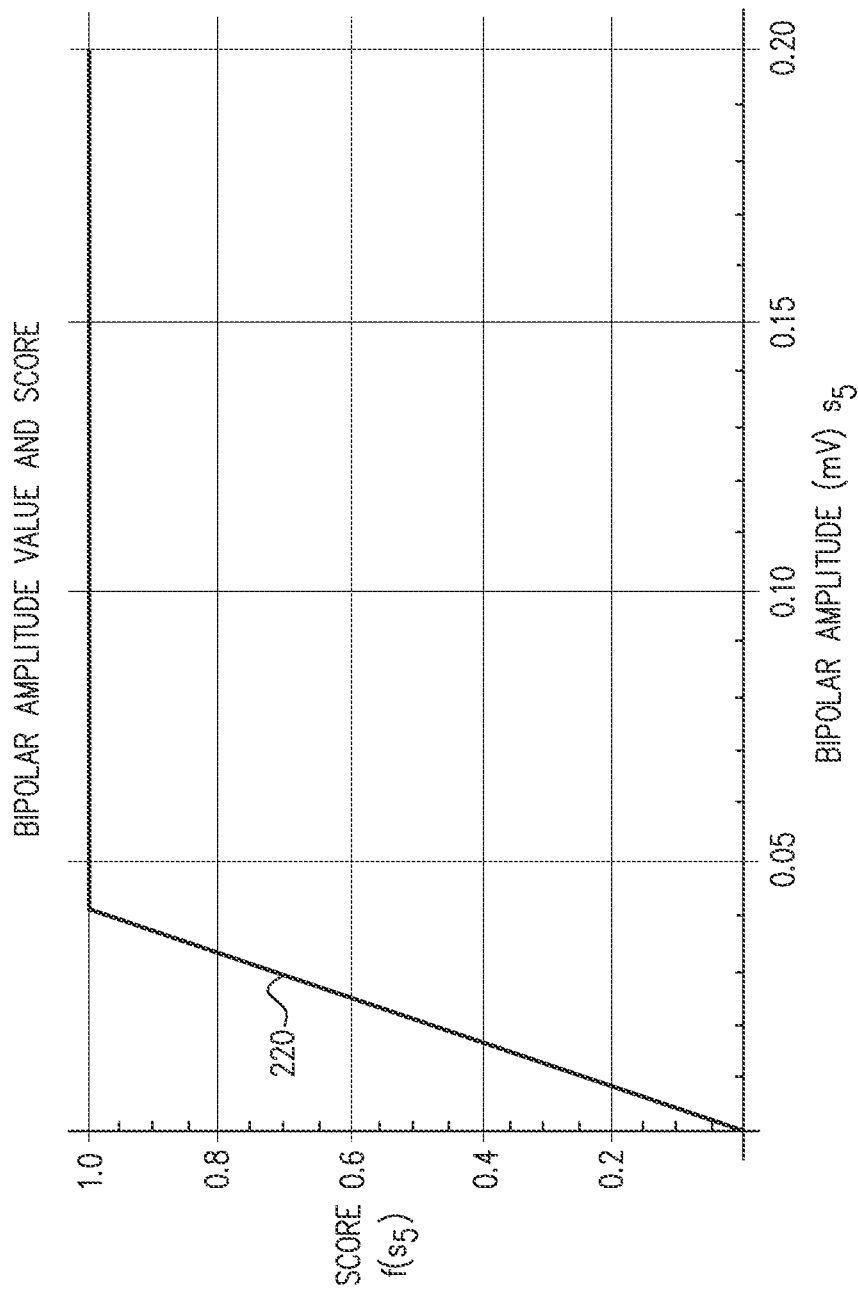
FIG. 16 is a graph of a bipolar amplitude fuzzy function, according to an embodiment of the present invention.

FIG. 16 is a graph 220 of a bipolar amplitude fuzzy function, according to an embodiment of the present invention. The bipolar amplitude within the unipolar activity segment (peak-to-peak), $s_2$, is also used for scoring the likelihood of the candidate annotations. The higher the value, the more likely that this is a true activation.

An equation for the fuzzy function is:

$$f(s_5) = 25 \cdot s_5, \ 0 \le s_5 \le 0.04; \ f(s_5) = 1, \ s_5 > 0.04 \quad (2)$$

where $s_5$ is the bipolar amplitude, and f($s_5$) is the score assigned to the amplitude.

The amplitude is calculated on the baseline rejected bipolar smoothed signal after low pass of Gaussian and anti-aliasing filter.

6. Final Score

As described above, each feature receives a score and the scores are used together in generating a global score. The idea is that features can support one another in inclusion or exclusion of an annotation. In one embodiment the score method which we used is defined as follows:

$$GS = \sqrt[5]{\prod_1^5 f(s_i)} \quad (3)$$

where GS is the global score.

The value of GS should pass a specific threshold, for example 0.8, for the annotation to be considered as valid.

It will be apparent to those skilled in the art that global scores, different from those exemplified above but having an equivalent outcome, can be used in embodiments of the present invention. Such global scores can include substantially any combination of weighted average of individual scores, and/or dot products of individual scores. Such global scores can also include a composition of scores based on a subset of fuzzy features. The scope of the present invention includes all such global scores.

Bipolar Amplitude Filtering

In some embodiments a final stage of the algorithm is designed to provide the user the ability to eliminate annotations that were detected if they have a low bipolar amplitude. The required amplitude threshold is controlled by the user. The bipolar amplitude filtering compares the bipolar amplitude of each annotation that surpassed the post processing stage with a threshold. Only annotations having a bipolar amplitude that exceeds the threshold are passed to the system. (If a user desires to skip this stage she/he may set the threshold to zero, thus eliminating the rule of this stage.)

The bipolar amplitude of each annotation is defined by measuring the peak-to-peak amplitude, baseline removed, 1 KHz bipolar signal in a 14 ms window centered around the annotation time (maximum unipolar velocity point). In one embodiment a system default value of bipolar amplitude threshold is set to 30 micro Volts.

This bipolar amplitude is different from the fuzzy controlled bipolar amplitude (described above), since this bipolar amplitude is determined on a fixed interval. The fuzzy classifier uses a dynamic segment of the unipolar activation and therefore in some embodiments the dynamic segment may be more meaningful as a classifier. In addition this classifier is used as a dichotomic user controlled threshold.

Algorithm Final Output

All annotations that pass the fuzzy score and the bipolar user controlled bipolar amplitude are considered valid annotations that may be used by the processor.

Figure 17:
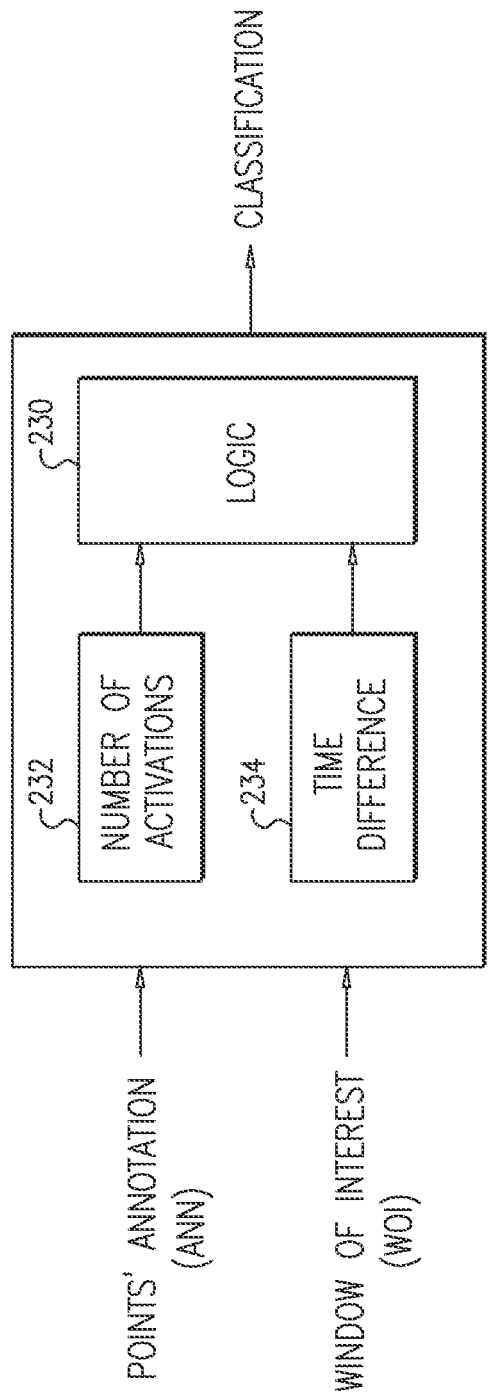
FIG. 17 is a schematic block diagram of a classification algorithm, according to an embodiment of the present invention.

In one embodiment each annotation should have the following features:

1. The annotation time index
2. The unipolar and bipolar derivative value
3. The fuzzy score
4. The unipolar detected downslope segment duration
5. The unipolar amplitude within that segment
6. The bipolar amplitude within that segment
7. The bipolar amplitude for the user controlled value In addition trace files may be provided, to include 1. The specific fuzzy score for each of the features
2. The unipolar segment start and end time index 2. Classification Algorithm FIG. 17 is a schematic block diagram of a classification algorithm, according to an embodiment of the present invention. The algorithm inputs consist of the ECG signal's annotation data that is derived from the wavefront annotation algorithm final output (the outputs are listed above), and a window of interest (WOI). The WOI may be any convenient time segment that includes the ECG signal, and is selected by the algorithm user, typically based on such factors as the tachycardia type and the mapping type. Additional inputs to the algorithm are described below with reference to FIG. 18.

A wavefront annotation is the position in time where the absolute value of the local unipolar signal slope is a minimum.

The data associated with each wavefront annotation contains the LAT (local activation time), local unipolar and bipolar slope (dv/dt) and a score value on the range 0-1, respectively corresponding to items 1, 2, and 3 of the wavefront annotation algorithm final output section. The score attribute establishes the likelihood of the annotation point being a correct annotation point. These attributes typically exist only in electro-anatomical activations that are detected using the wavefront algorithm.

FIG. 17 illustrates that the classification algorithm applies, in a logic block 230, a number of activations and a time difference between the activations as illustrated by respective blocks 232 and 234. Actions performed in the logic block are described below with reference to FIG. 18.

Figure 18:
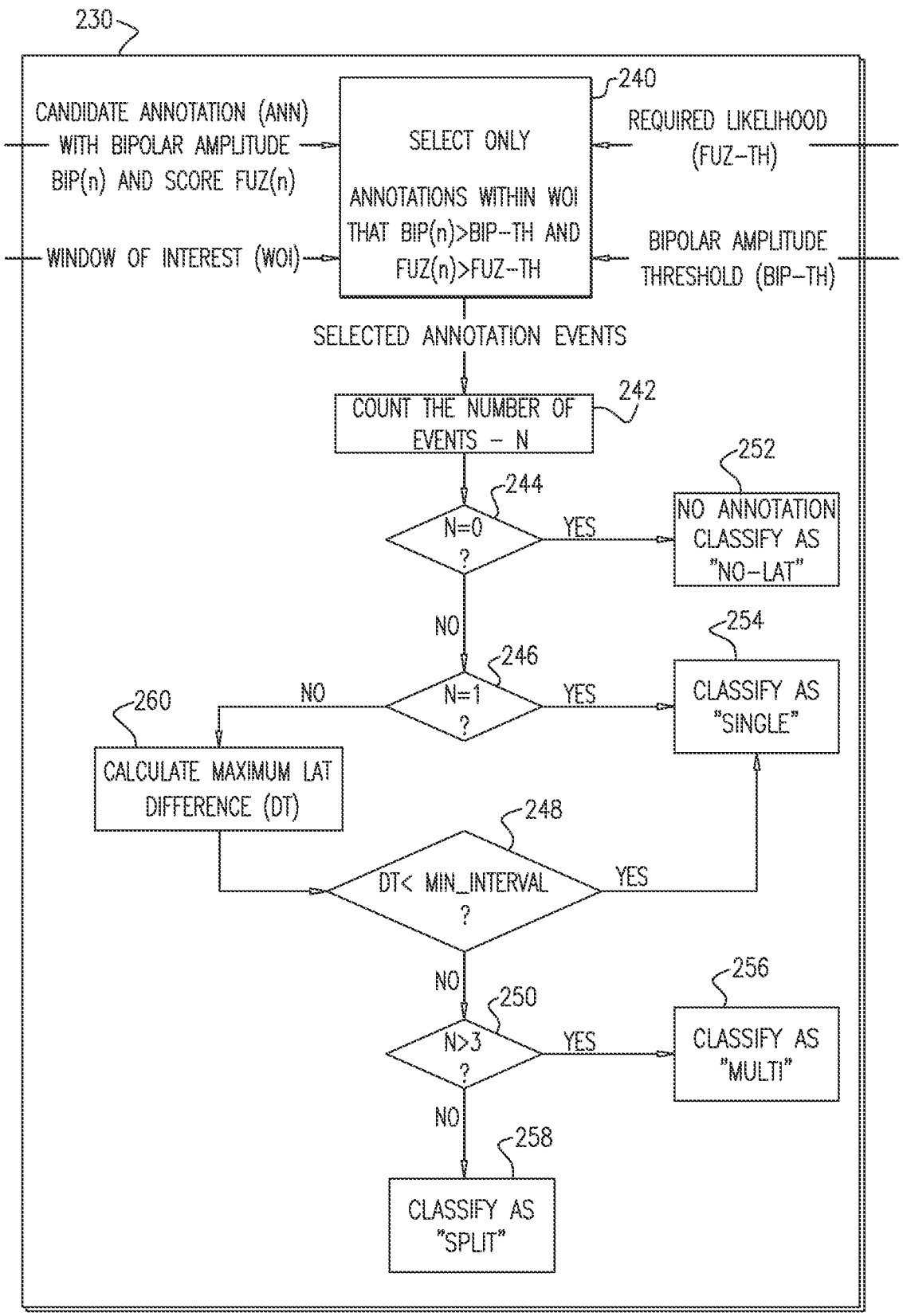
FIG. 18 is a flowchart showing steps of the classification algorithm, according to an embodiment of the present invention.

FIG. 18 is a flowchart showing steps of the classification algorithm performed in logic block 230, according to an embodiment of the present invention. In addition to the inputs described above, additional inputs to the algorithm are shown in FIG. 18. These inputs are:

1. A minimum required bipolar amplitude. Each annotation point must exceed a threshold value (Bip-Th) to be considered as a valid point for the enumeration.

2. A minimum required likelihood score. Each annotation point score value must exceed a threshold (Fuz-Th) value in order to be considered as a valid point for the enumeration process. The score value may be different for each mapping chamber (Ventricular/Atria).

3. A minimum required activation time, min interval, for complex classification. This value is used when two or more valid activations exist in the WOI. If the time interval between the earliest to the latest activation is smaller than this threshold value the activation will be classified as a single event, otherwise it will be classified as either split or multi depending on the number of activations within the WOI.

While the description above assumes one value for the min interval, embodiments of the present invention include the option of selecting different values of min interval for different anatomic regions originating the ECG signal. In addition, the WOI may dynamically change. Also, the ECG signals analyzed may be limited to those either below or above a specific bipolar amplitude, or to those that have mixed amplitudes (at least one above some value and at least another below some other value).

In a selection block 240, only annotations within the WOI, and where the following expression is true, are selected:

Bip(n)>Bip-Th AND Fuz(n)>Fuz-Th

The selected annotations are counted in a counting block 242, to give a number N, and the group of selected annotations are then classified in four comparisons 244, 246, 248, and 250.

Comparison 244 checks if N=0, in which case the group is classified as No-Lat in a first classification block 252.

Comparison 246 checks if N=1, in which case the group is classified as "Single" in a second classification block 254. If comparison 246 returns negative, a further calculation of a maximum LAT difference DT is made in a calculation block 260, and if, in comparison 248 DT<min interval, the annotations are treated as being one annotation, and the group is also classified as Single in block 254.

If comparison 248 returns negative there are two or more assumed annotations, and these are classified in comparison 252, which checks if N>3. If comparison 252 returns positive, the group is classified as Multi in a third classification block 256. If comparison 252 returns negative, in the case of N=2 or N=3, the group is classified as Split in a fourth classification block 258.

The classification results may typically be presented to the algorithm user on a display screen, such as display screen 450 referred to in the description of FIG. 23 below.

EXAMPLES

We present below several examples of unipolar and bipolar signals along with the annotations input and the WOI input. Each example includes an explanation of the expected complex point classification. While the examples described have two unipolar signals, a distal and a proximal signal, it will be understood that the algorithm described herein only requires one unipolar signal.

Figure 19:
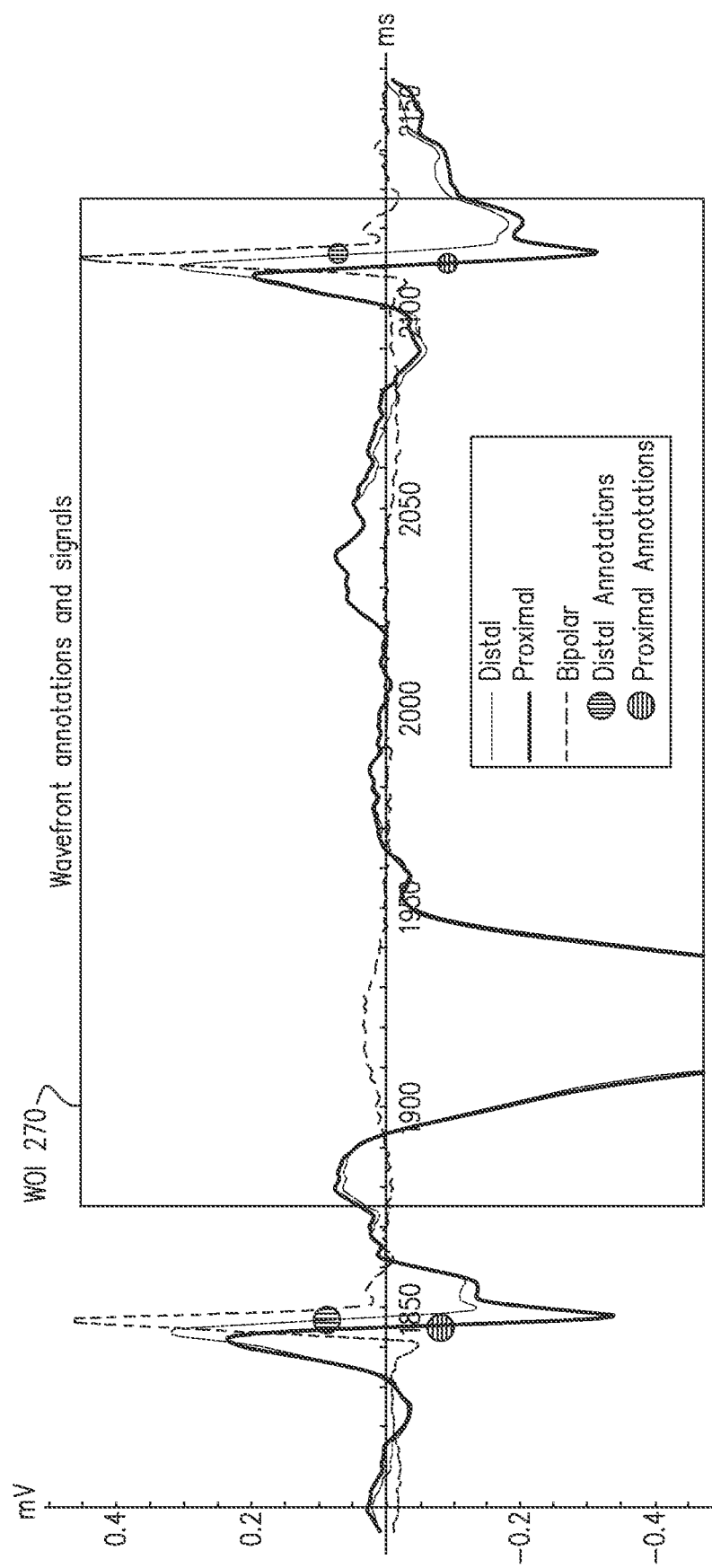
FIG. 19 illustrates a single event classification, according to an embodiment of the present invention.

FIG. 19 illustrates a single event classification, according to an embodiment of the present invention. The figure shows separate distal and proximal unipolar signals with the input annotations to the classification algorithm marked. A rectangle 270 marks the window of interest (WOI) wherein the algorithm operates. Other annotations outside the WOI do not contribute to the classification.

Both the distal and the proximal electrodes have a single annotation event in the region of interest, thus resulting in a classification of "single event" for each of the electrodes.

Figure 20:
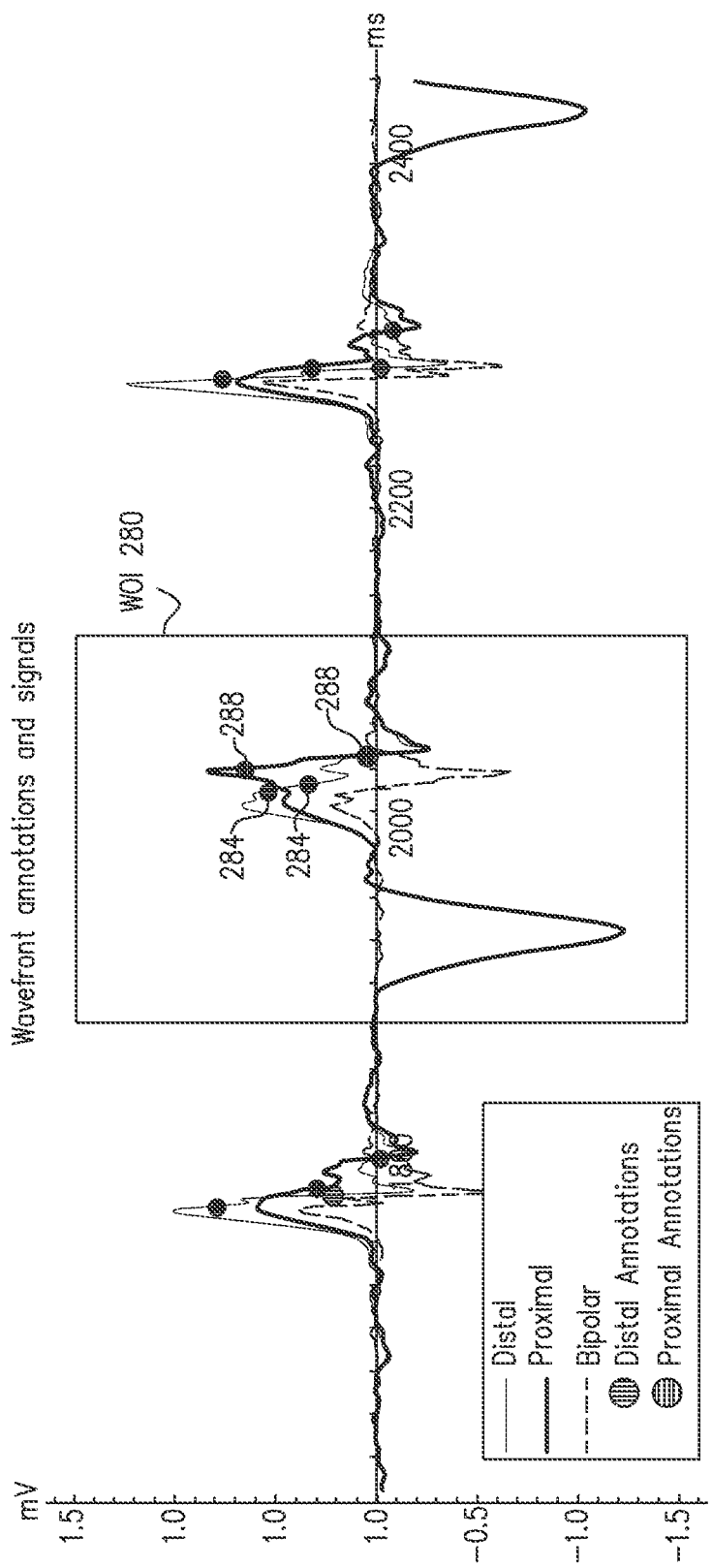
FIG. 20 illustrates the effect of annotation times on the classification, according to an embodiment of the present invention.

FIG. 20 illustrates the effect of annotation times on the classification, according to an embodiment of the present invention. As for FIG. 19, a rectangle 280 marks the window of interest (WOI) wherein the algorithm operates. Other annotations outside the WOI do not contribute to the classification.

The distal annotations have two consecutive events that are very close time wise and that are marked in the WOI with two points 284, thus resulting in a classification of "single event". In this case the flow through the flowchart is N=1? No; Calculate Maximum LAT Difference (DT); DT<min interval? Yes.

The proximal annotations, points 288, are further apart, thus resulting in classification of "split event". In this case the flow through the flowchart is N=1? in comparison 246 No; Calculate Maximum LAT Difference (DT) in block 260; DT<min interval? in comparison 248 No; N>3? In comparison 250 No.

Figure 21:
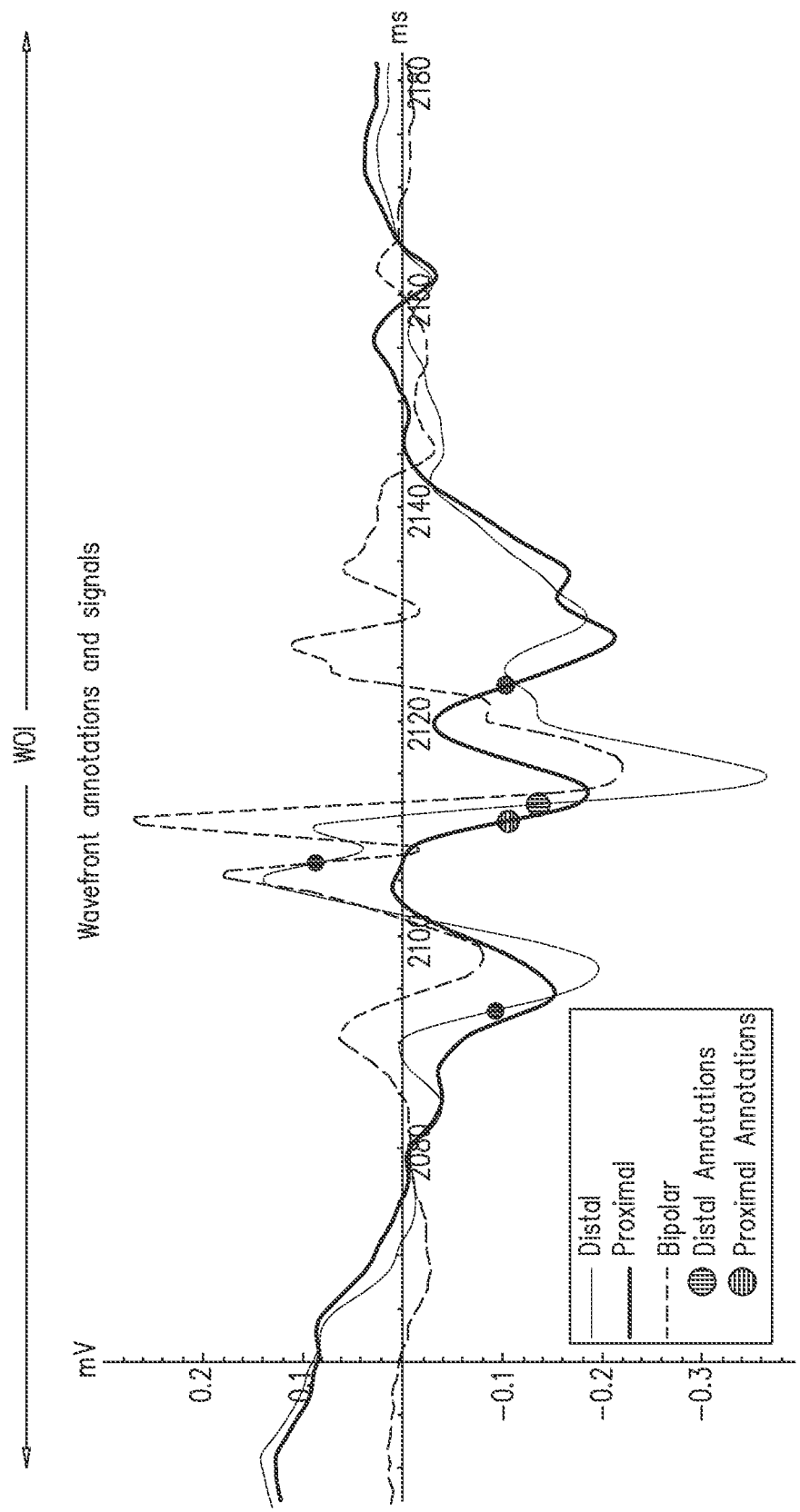
FIG. 21 illustrates a split classification, according to an embodiment of the present invention.

FIG. 21 illustrates a split classification, according to an embodiment of the present invention. For this example, the WOI is assumed to cover the entire signal shown. In this case both electrodes will be classified here as split, since the time difference (for each electrode separately) between the earliest and latest activity is longer than the "min interval" parameter of the flowchart (FIG. 18). The classification to split is because the number of annotations in the distal electrode is three and for the proximal electrode it is two respectively. In both cases the flowchart arrives to N>3?, and in both cases the answer, being fewer than 4 annotations, is No.

Figure 22:
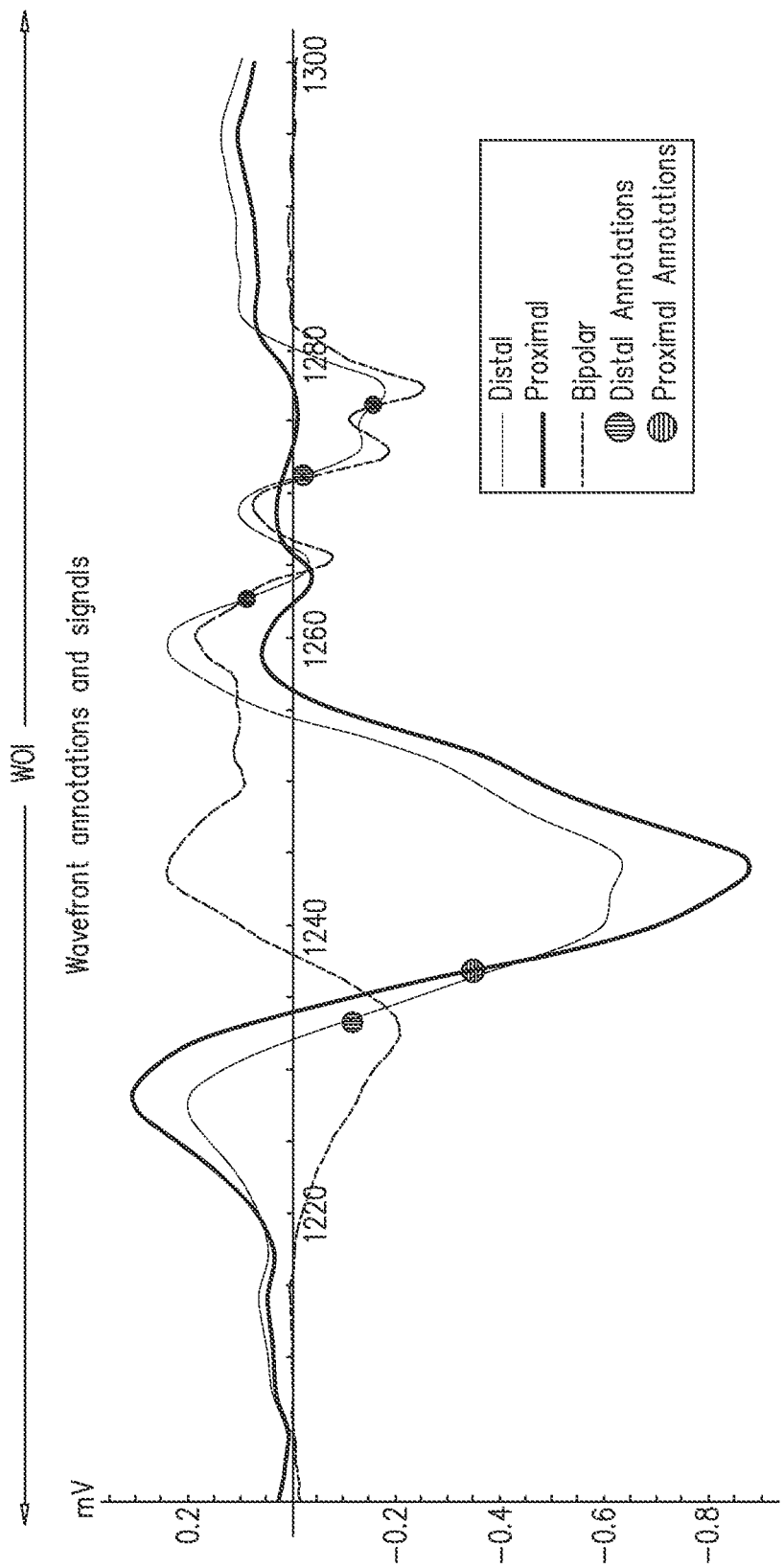
FIG. 22 illustrates a multi classification, according to an embodiment of the present invention.

FIG. 22 illustrates a multi classification, according to an embodiment of the present invention. As for FIG. 21 the WOI is assumed to cover the entire signal shown. In this case the distal electrode will be classified as "Multi" since the number of annotations is larger than 3 and since the time difference between the earliest and latest activity is longer than the "min interval" parameter of the flowchart. The Proximal electrode in this case will be classified as a single event.

The final classification can further be based on a check of consistency between consecutive beats. When considering any specific beat in a WOI the previous several beats (typically one or two previous beats) can be used. Each previous beat receives individually its classification as explained previously, relative to its WOI, while the final classification of a current beat will be based on majority voting, where the different classifications may be assigned relative weights. For example, single may have a higher weight than multi, which in turn has a higher weight than split. In this case, if the current beat is classified as split but the previous one is classified as single then the final classification of the current beat will not be split but rather single.

While this is the most basic form of consistency, additional consistency measures apparent to those having ordinary skill in the art may include morphology matching of unipolar or bipolar signals or time events analysis between beats. All such consistency measures are included within the scope of the present invention.

FIG. 23 is a schematic illustration of an invasive medical procedure using an apparatus 400, according to an embodiment of the present invention. The procedure is performed by a medical professional 402, and, by way of example, the procedure in the description hereinbelow is assumed to comprise acquisition of ECG signals from a heart 404 of a human patient 406.

In order to acquire the signals, professional 402 inserts a probe 408 into a sheath 410 that has been pre-positioned in a lumen of the patient. Sheath 410 is positioned so that a distal end 412 of the probe may enter the heart of the patient, after exiting a distal end 414 of the sheath, and contact tissue of the heart.

Probe 408 may comprise any type of catheter that can be inserted into the heart of the patient, and that can be tracked, typically using a magnetic tracking system and/or an impedance measuring system. For example, probe 408 may comprise a lasso catheter, a shaft-like catheter, or a pentaRay catheter, produced by Biosense Webster of Diamond Bar, Calif., or catheters generally similar to these catheters. Biosense Webster also produces a magnetic tracking system and an impedance measuring system that may be used in embodiments of the present invention.

Probe 408 comprises at least two electrodes 411, which are used to acquire the ECG signals used by processor 20 in performing the algorithms described herein.

Apparatus 400 is controlled by processor 20 (FIG. 1), and the processor may comprise real-time noise reduction circuitry 420, typically configured as a field programmable gate array (FPGA), followed by an analog-to-digital (A/D) signal conversion integrated circuit 424. The processor can pass the signal from ND circuit 424 to another processor and can be programmed to perform the algorithms disclosed herein.

Processor 20 is located in an operating console 430 of the apparatus. Console 430 comprises controls 432 which are used by professional 402 to communicate with the processor. During the procedure, processor 20 communicates with an ECG module 436 in a module bank 440, in order to acquire ECG signals as well as to perform the algorithms disclosed herein.

ECG module 436 receives ECG signals from electrode 411. In one embodiment the signals are transferred, in module 436, through a low noise pre-amplifier 438, and via a band pass filter 440, to a main amplifier 442. Module 436 also comprises an analog to digital converter (ADC) 444, which transfers digitized values of the ECG signals to processor 20, for implementation by the processor of the algorithms described herein. Typically, processor 20 controls the operation of pre-amplifier 438, filter 440, amplifier 442, and ADC 444.

Thus, ECG module 436 enables processor 20 to acquire and analyze EP (electrophysiological) signals received by electrode 411, including the ECG signals referred to herein. The signals are typically presented to professional 402 as voltage-time graphs, which are updated in real time, on a display screen 450.

The software for processor 20 and module bank 440 may be downloaded to the processor in electronic form, over a network, for example. Alternatively or additionally, the software may be provided on non-transitory tangible media, such as optical, magnetic, or electronic storage media.

In order to operate apparatus 12, module bank 50 typically comprises modules other than the ECG module described above, such as one or more tracking modules allowing the processor to track the distal end of probe 408. For simplicity, such other modules are not illustrated in FIG. 1. All modules may comprise hardware as well as software elements.

In addition to display screen 450 presenting ECG signals acquired by electrode 411, results 452 of the algorithms described herein may also be presented to the algorithm user on the display screen.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus, comprising:
a pair of electrodes configured to be placed in proximity to a myocardium of a human subject; and
a processor configured to:
receive a bipolar signal from the pair of electrodes,
receive a unipolar signal with a unipolar feature from a selected one of the pair of electrodes;
delineate a window of interest (WOI) representative of a time interval for the unipolar and bipolar signals;
within the WOI compute local unipolar minimum derivatives of the unipolar signal and times of occurrence of the local unipolar minimum derivatives;
within the WOI compute bipolar derivatives of the bipolar signal at the times of occurrence;
evaluate ratios of the bipolar derivatives to the local unipolar minimum derivatives;
evaluate the bipolar feature and the unipolar feature using at least one fuzzy function to provide a score representative of a confidence value, wherein the fuzzy function evaluates a ratio of unipolar duration to amplitude of the unipolar signal, and an amplitude of the bipolar signal;
when the ratios are greater than a preset threshold ratio value and the score exceeds a preset threshold score value, assign the times of occurrence as times of activation of the myocardium;
count a number of the times of activation; and
classify the unipolar signal as one selected from the group consisting of a no activation event, a split event, a single activation event and a multiple activation event, according to the number;
a filter configured to minimize interferences in the bipolar signal and the unipolar signal prior to computation of the local unipolar minimum derivatives and the bipolar derivatives; and
wherein in a split event, the processor is configured to eliminate a weaker feature of a pair of features of the unipolar signal when respective annotations of the pair of features are within a 50 ms time window.

2. The apparatus of claim 1, wherein the fuzzy function includes a unipolar duration fuzzy function.

3. The apparatus of claim 1, wherein the fuzzy function includes a unipolar amplitude fuzzy function.

4. The apparatus of claim 1, wherein the fuzzy function includes a unipolar duration to amplitude ratio fuzzy function.

5. The apparatus of claim 1, wherein the processor is configured to assign the times of occurrence as the times of activation of the myocardium when the bipolar derivatives are less than a preset bipolar derivative threshold.

6. The apparatus of claim 1, wherein the processor is configured to classify the unipolar signal comprises defining a plurality of preset classifications for the unipolar signal.

7. The apparatus of claim 6, wherein the plurality comprises a first classification wherein the number is zero, a second classification wherein the number is one, a third classification wherein the number is two or three, and a fourth classification wherein the number is greater than three.

8. The apparatus of claim 1, wherein the processor is configured to assign a given time of occurrence as a given time of activation of the myocardium when a confidence level associated with the given time of occurrence is greater than a preset confidence level.

9. The apparatus of claim 8, wherein the processor is configured to solely assign the given time of occurrence as the given time of activation of the myocardium when an amplitude of a corresponding bipolar signal is greater than a preset bipolar signal threshold.

\* \* \* \* \*